United States Patent
Nishida et al.

(12) 
(10) Patent No.: US 6,221,899 B1
(45) Date of Patent: Apr. 24, 2001

(54) TERPENOID LACTONE COMPOUNDS AND THEIR PRODUCTION PROCESS

(75) Inventors: Hiroyuki Nishida, Handa; Masaya Ikunaka, Kobe; Nobuji Yoshikawa, Anjo; Katsuomi Ichikawa, Okazaki; Nakao Kojima, Nagoya, all of (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/596,728

(22) Filed: Jun. 16, 2000

Related U.S. Application Data

(62) Division of application No. 09/232,080, filed on Jan. 15, 1999.

(51) Int. Cl.$^7$ .......................... A61K 31/35; A61K 31/44
(52) U.S. Cl. .......................... 514/454; 455/557; 455/290
(58) Field of Search .................................. 514/454, 455, 514/290, 557

(56) References Cited

FOREIGN PATENT DOCUMENTS 0098041    1/1984   (EP) .

OTHER PUBLICATIONS

Jane Wu Won, et al., Tetrahedron, vol. 36, No. 29, pp. 5255–5256, 1995.
Daniel Hwang, et al, 1996, 226(3), 810–818, XP–002104592.
I. H. Hall et al, Jrnl of Pharm Sciences, vol. 68, No. 5, May 1979, pp. 534–542, XP–002104593.
Alejandro Barrero, et al., Tetrahedron Let. 36, pp. 5251–5254, 1995.
Tetrahedron Let., vol. 25, No. 4 pp. 469–472, 1984.
Katakami et al., Immunology, 1988, 64, 719–724.
Badger et al., Circul. Shock, 1994, 44, 188–195.
Mohler et al., Nature, 1994, 370, 218–220.
Sampaio et al., J. Exp. Med, 1991, 73, 699–703.

*Primary Examiner*—Amelia Owens
(74) *Attorney, Agent, or Firm*—Peter C. Richardson; Gregg C. Benson; Gabriel L. Kleinman

(57) ABSTRACT

This invention provides terpenoid lactone compounds, and processes for producing the terpenoid lactone compounds, which comprise cultivating *Oidiodedron griseum* FERM BP-5778 and then isolating the terpenoid lactone compounds from the fermentation broth. The present invention also provides a pharmaceutical composition comprising the teipenoid lactone compound, which is useful in the treatment of IL-1 and TNF mediated diseases or the like.

1 Claim, No Drawings

TERPENOID LACTONE COMPOUNDS AND THEIR PRODUCTION PROCESS

CROSS-REFERENCE TO RELATED APPLICATIONS

This is a division of copending U.S. Ser. No.09/232,080, filed Jan. 15, 1999, entitled "Terpenoid Lactone Compounds And Their Production Process", which claims priority to International Application No. PCT/IB98/00110 filed Jan. 29, 1998.

TECHNICAL FIELD

This invention relates to terpenoid lactone compounds and particularly to terpenoid lactone compounds produced by fermentation of an fungus *Oidiodendron griseum,* which has been deposited as FERM BP-5778. This invention also relates to processes for producing the terpenoid lactone compounds, and a pharmaceutical composition comprising the same, which is useful in the treatment of IL-1 and TNF mediated diseases.

BACKGROUND ART

Interleukin-1 (IL-1) and tumor necrosis factor (TNF) are biological substances produced by a variety of cells, such as monocytes or macrophages. The IL-1 and TNF have been demonstrated to mediate a variety of biological activities thought to be important in immunoregulation and other physiological conditions such as inflammation.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic b cells. The only IL-1 blocker available today is the natural IL-1 receptor antagonist (IL-1RA), a polypeptide which is easily metabolized in the bloodstream with a very short half-life. Thus, active research has been carried out to develop stable, long-acting agents which can be taken by oral administration or by parenteral injections rather than by intravenous infusion, which is required for IL-1RA. A number of compounds as IL-1 receptor antagonists, IL-1 biosynthesis inhibitors, and IL-1 converting enzyme inhibitors have been claimed.

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, acquired immunodeficiency syndrome (AIDS), AIDS related complex (ARC), keloid formation, scar tissue formation, Crohn's disease, ulcerative colitis, or pyresis. Although significant progress in developing potent TINF modulators has been achieved through the use of recombinantly derived proteins including monoclonal antibodies and soluble receptors, the development of biosynthesis inhibitors and antagonists has been less successful.

Recently a number of small molecule TNF modulators have been claimed. Most of them which specifically inhibit TNF production do so by increasing intracellular cyclic adenosine monophosphate (cAMP) which ultimately blocks TNF gene expression (Y. KATAKAMI et al., *Immunology,* 1988, 64, 719). The most important of these compounds are the rolipram and pentoxifylline-relared phosphodiesterase IV (PDE IV) inhibitors which are being activity pursued by a number of pharmaceutical companies (A. BADGER et al., *Circul. Shock,* 1994, 44, 188). The ability of thalidomide to block TNF production contributes to its therapeutic properties in humans (E. P. SAMPAIO et al., *J Exp. Med,* 1991, 73, 699). Recent studies suggest that cell-associated TNF may be necessary for normal host defense mechanisms. This finding has added to the excitement concerning the identification of a unique metalloproteinase enzyme which is responsible for the proteolytic processing of TNF. Inhibitors of matrix metalloproteinase-related enzyme have appeared (K. M. MOHLER et al., *Nature,* 1994, 370, 218).

The object of the present invention is to provide the terpenoid compounds having an excellent activities for ThF and/or IL-1 biosynthesis inhibition and a pharmaceutical composition comprising the same. Another object is to provide processes for producing the terpenoid compounds.

BRIEF DESCLOSURE OF THE INVENTION

Accordingly, the present invention provides novel terpenoid compounds of the following formula:

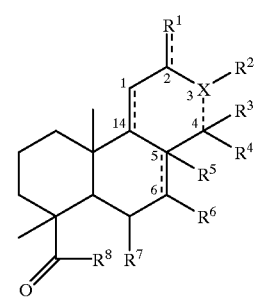

(I)

wherein the dotted line is an optional bond;
$R^1$ is O or OH;
X is O or N, or absent;
$R^2$ is H, $C_1$–$C_5$ alkyl, or benzyl or absent;
$R^3$ is H, OH, $C_1$–$C_4$ alkoxycarbonyl-$C_1$–$C_3$ alkyl, $C_1$–$C_4$ alkoxycarbonyl-$C_1$–$C_3$ alkenyl, $C_1$–$C_4$ alkoxy or $C_1$–$C_4$ alkylthio;
$R^4$ is H or $C_1$–$C_5$ alkoxy;
$R^5$ is H, $C_1$–$C_4$ alkylthio or $C_1$–$C_4$ alkoxycarbony-$C_1$–$C_4$ alkylthio or absent;
$R^6$ is H or OH; or
$R^5$ and $R^6$ form, together with the carbon atom to which they are attached, an oxirane ring;
$R^7$ is H;
$R^8$ is OH; or
$R^7$ and $R^8$ form, together with the carbon to which they are attached, a lactone ring; with proviso that
when X is O and $R^2$ is absent, the dotted line between 3- and 4-positions is a single bond;
when $R_5$ is absent, $R^7$ is H and $R^8$ is OH; and
when $R^1$ is O; and $R^5$ and $R^6$ form, together with the carbon atom to which they are attached, an oxirane ring; $R^3$ is not methoxy.

The present invention also provides a culture of *Oidiodedron griseum.* which is capable of producing the terpenoid compounds.

Further, the present invention provides a process for producing the terpenoid compounds of formulas (I) which comprises cultivating a microorganism having identifying characteristics of FERM BP-5778, or a mutant or recombinant form thereof, and, if required, isolating terpenoid lactone compounds from the fermentation broth.

Also, the present invention provides a pharmaceutical composition for use in the treatment of IL-1 and TNF mediated diseases, which comprises the terpenoid compounds of formulas (I) and a pharmaceutically acceptable carrier.

Also, the present invention provides a method for the treatment of IL-1 and TNF mediated diseases, which comprises administering to said subject an antiinflammation amount of the compounds of formulas (I) and a pharmaceutically acceptable carrier.

DETAILED DESCRIPTION OF THE INVENTION

Preferred compounds of this invention include a compound of formula (I) wherein $R^1$ is O; X is O; $R^2$ is absent; $R^3$ is OH; $R^4$ is H; $R^5$ and $R^6$ form, together fth carbon to which they are attached, an oxirane ring; and $R^7$ and $R^8$ form, together Keith carbon to which they are attached, a lactone ring ([5bS-(1aR*,5bβ,8aα,8bα,10aα,10bβ)]-5b,6,7,8,8a,8b, 10a,10b-octahydro-2-hydroxy-5b,8a-dimethyl-2H,4H,9H-furo[2',3',4':4,5]oxireno[2,3]naphtho[2,1-c]pyran-4,9-dione);

a compound of formula (I) wherein $R^1$ is O; X is O; $R^2$ is absent; $R^3$ is H; $R^4$ is H; $R^5$ and $R^6$ form, together with carbon to which they are attached, an oxirane ring; and $R^7$ and $R^8$ form, together with carbon to which they are attached, a lactone ring ([5bS-(1aR*,5bβ,8aα,8bα,10aα,10bβ)]-5b,6,7,8,8a,8b,10a, 10b-octahydro-5b,8a-dimethyl-2H,4H,9H-furo[2',3',4':4,5]oxireno[2,3]naphtho[2,1-c]pyran-4,9-dione);

a compound of formula (I) wherein $R^1$ is O; X is O; $R^2$ is absent; $R^3$ is methoxycarbonylmethyl; $R^4$ is H; $R^5$ and $R^6$ form, together with carbon to which they are attached, an oxirane ring; and $R^7$ and $R^8$ form, together with carbon to which they are attached, a lactone ring ([5bS-(1aR*,5bβ,8aα,8bα,10aα,10bβ)]-5b,6,7,8,8a,8b,10a,10bβ)]-5b,6,7,8,8a,8b,10a,10b-octahydro-2-methoxycarbonylmethyl-5b,8a-dimethyl-2H,4H,9H-furo[2',3',4':4,5]oxireno[2,3]naphtho[2,1 -c]pyran-4,9-dione);

a compound of formula (I) wherein $R^1$ is O; X is O; $R^2$ is absent; $R^3$ is methoxy; $R^4$ is H; $R^5$ and $R^6$ form, together with carbon to which they are attached, an oxirane ring; and R7 and $R^8$ form, together with carbon to which they are attached, a lactone ring ([2R-(1aR*,2β,5bβ,8aα,8bα,10aα,10bβ)]-5b,6,7,8,8a,8b,10a,10b-octahydro-2-methoxy-5b,8a-dimethyl-2H,4H,9H-furo[2',3',4':4,5]oxireno[2,3]naphtho[2,1-c]pyran-4,9-dione);

a compound of formula (I) wherein $R^1$ is O; X is O; $R^2$ is absent; $R^3$ is methoxy; R4 is H; $R^5$ is ethoxycarbonylethylthio; $R^6$ is OH; and $R^7$ and $R^8$ form, together with carbon to which they are attached, a lactone ring ([3aS-(3aα,5aα,6aα,7aα,10bβ,10cα)]-1,2,3,3a,5a,6,6a,7,10b,10c-decahydro-6-hydroxy-6a-(2-ethoxycarbonyl-1-ethylthio)-7-methoxy-3a,10b-dimethyl-4H,9H-furo[2',3',4':4,5]naphtho[2,1-c]pyran-4,9-dione); and a compound of formula (I) wherein $R^1$ is O; X is O; $R^2$ is H; $R^3$ is methoxycarbonylethylene; $R^4$ is H; $R^5$ and $R^6$ form, together with carbon to which they are attached, an oxirane ring; and $R^7$ and $R^8$ form, together with carbon to which they are attached, a lactone ring ([2aS-(1aR*,2aβ,5aα,5bα,7aα,7bβ)]-2a,3,4,5,5a,5b,7a,7b-octahydro-1a-{2-methoxycarbonyl-1-(E)-ethenyl}-2a,5a-dimethyl-1aH,6H-furo[2',3',4':4,5]oxireno[2,3]-(E)-(1-naphthalenylidene)acetic acid-6-one).

More preferred compounds of this invention include a compound of formula (I) wherein $R^1$ is O; X is O; $R^2$ is absent; $R^3$ is OH; $R^4$ is H; $R^5$ and $R^6$ form, together with carbon to which they are attached, an oxirane ring; and $R^7$ and $R^8$ form, together with carbon to which they are attached, a lactone ring ([5bS-(1aR*,5bβ,8aα,8bα,10aα,10bβ)]-5b,6,7,8,8a,8b,10a,10b-octahydro-2-hydroxy-5b,8a-dimethyl-2H,4H,9H-furo[2',3',4':4,5]oxireno[2,3]naphtho[2,1-c]pyran-4,9-dione);

a compound of formula (I) wherein $R^1$ is O; X is O; $R^2$ is absent; $R^3$ is H; $R^4$ is H; $R^5$ and $R^6$ form, together with carbon to which they are attached, an oxirane ring; and $R^7$ and $R^8$ form, together with carbon to which they are attached, a lactone ring ([5bS-(1aR*,5bβ,8aα,8bα,10aα,10bβ)]-5b,6,7,8,8a,8b,10a,10b-octahydro-5b,8a-dimethyl-2H,4H,9H-furo[2',3',4':4,5]oxireno[2,3]naphtho[2,1-c]pyran-4,9-dione); and a compound of formula (I) wherein $R^1$ is O; X is O; $R^2$ is absent; $R^3$ iS methoxycarbonylmethyl; $R^4$ is H; $R^5$ and $R^6$ form, together with carbon to which they are attached, an oxirane ring; and $R^7$ and $R^8$ form, together with carbon to which they are attached, a lactone ring ([5bS-(1aR*,5bβ,8aα,8bα,10aα,10bβ)]-5b,6,7,8,8a,8b,10a,10b-octahydro-2-methoxycarbonylmethyl-5b,8a-dimethyl-2H,4H,9H-furo[2',3',4':4,5]oxireno[2,3]naphtho[2,1-c]pyran-4,9-dione).

Preferred individual compounds of this invention are:
[5bS-(1aR*,5bβ,8aα,8bα,10aα,10bβ)]-5b,6,7,8,8a,8b,10a,10b-octahydro-2-hydroxy-5b,8a-dimethyl-2H,4H,9H-furo[2',3',4':4,5]oxireno[2,3]naphtho[2,1-c]pyran-4,9-dione;
[5bS-(1aR*,5bβ,8aα,8bα,10aα,10bβ)]-5b,6,7,8,8a,8b,10a,10b-octahydro-5b,8a-dimethyl-2H,4H,9H-furo[2',3',4':4,5]oxireno[2,3]naphtho[2,1-c]pyran-4,9-dione;
[5bS-(1aR*,5bβ,8aα,8bα,10aα,10bβ)-5b,6,7,8,8a,8b,10a,10b-octahydro-2-methoxycarbonylmethyl-5b,8a-dimethyl-2H,4H,9H-furo[2',3',4':4,5]oxireno[2,3]naphtho[2,1-c]pyran-4,9-dione;
[2R-(1aR*,2β,5bβ,8aα,8bα,10aα,10bβ)]-5b,6,7,8,8a,8b,10a,10b-octahydro-2-methoxy-5b,8a-dimethyl-2H,4H,9H-furo[2',3',4':4,5]oxireno[2,3]naphtho[2,1-c]pyran-4,9-dione;
[3aS-(3aα,5aα,6α,7α,10bβ,10cα)]-1,2,3,3a,5a,6,6a,7,10b,10c-decahydro-6 -hydroxy-6a-(2-ethoxycarbonyl-1-ethylthio)-7-methoxy-3a,10b-dimethyl-4H,9H-furo[2',3',4':4,5]naphtho[2,1-c]pyran-4,9-dione; and
[2aS-(1aR* ,2aβ,5aα,5bα,7aα,7bβ)]-2a,3,4,5,5a,5b,7a,7b-octahydro-1a-{2-methoxycarbonyl-1-(E)-ethenyl}-2a,5a-dimethyl-1aH,6H-furo[2',3',4':4,5]oxireno[2,3]-(E)-(1-naphthalenylidene)acetic acid-6-one.

Particularly preferred individual compounds are:
[5bS-(1aR*,5bβ,8aα,8bα,10aα,10bβ)]-5b,6,7,8,8a,8b,10a,10b-octahydro-2-hydroxy-5b,8a-dimethyl-2H,4H,9H-furo[2',3',4':4,5]oxireno[2,3]naphtho(2,1-c]pyran-4,9-dione;
[5bS-(1aR*,5bβ,8aα,8bα,10aα,10bβ)]-5b,6,7,8,8a,8b,10a,10b-octahydro-5b,8a-dimethyl-2H,4H,9H-furo[2',3',4':4,5]oxireno[2,3]naphtho[2,1-c]pyran-4,9-dione; and
[5bS-(1aR*,5bβ,8aα,8bα,10aα,10bβ)]-5b,6,7,8,8a,8b,10a,10b-octahydro-2-methoxycarbonylmethyl-5b,8a-dimethyl-2H,4H,9H-furo[2',3',4':4,5]oxireno[2,3]naphtho[2,1-c]pyran-4,9-dione.

The microorganism designated *Oidiodendron griseum* which is useful for the preparation of compounds of formula (I) was isolated from soil collected in Tsu, Mie, Japan. It has been deposited as FERM BP-5778 at National Institute of Bioscience and Human-Technology, Agency of Industrial Science and Technology (located at 1-3 Higashi 1-chome, Tsukuba, Ibaraki 305, Japan) under the Budapest Treaty on December 24, 1996.

The culture was single-block or smear inoculated from a block or a spore suspension of malt extract agar slant onto plates of identification media, and the plates were incubated at 25° C. for up to two weeks under complete darkness. The results were read at 14 days for cultural characteristics and temperature studies. The colors were determined by comparisons with color chips from Color Standards and Color Nomenclature by Robert Ridgway, 1912.

Identification media used for the characteristics of the strain and references describing their compositions are as follows:
1. Cornmeal Agar: Carmichael, J. W. 1957. Mycologia 49: 820–830.
2. Czapek-Sucrose Agar: Raper, K. B. and D. I. Fernell. 1965. The Genus Aspergillus, Baltimore, The Williams & Wilkins, p. 36.
3. Malt Extract Agar: Ibid, p. 38.
4. Glucose Agar: glucose 50 g, monobasic potassium phosphate 1 g, magnesium sulfate 0.5 g, potassium nitrate 2 g, agar 20 g, distilled water 1 L.
5. Oatmeal Agar: oatmeal 30 g, agar 15 g, distilled water 1 L.
6. Phytone Yeast Extract Agar: BBL.
7. Potato Dextrose Agar: Peeled potato 100 g, dextrose 10 g, agar 20 g, tap water 1 L.
8. V-8 Juice Agar: ATCC medium 343, ATCC Media Handbook, 1984, p. 17.
9. Temperature study: malt extract agar.

Culture FERM BP-5778 exhibited the following Characteristics:

Malt Extract Agar—Colonies attaining 2.5 cm diam., growth moderate, olive-gray to deep olive-gray (LI); velvety, thin, smooth, sporulation good; reverse blackish mouse gray, olivaceous black (3) (LI) to black; no soluble pigment.

Cornmeal Agar—Colonies attaining 2.5 cm diam., growth poor to moderate, olive-gray to deep olive-gray (LI); velvety, thin, smooth, sporulation good; reverse olivaceous black (1) (XLVI) to black; no soluble pigment.

Czapek-Dox Agar—Colonies attaining 3.0 cm diam., growth moderate, andover green (XLVII), light olive-gray to olive-gray (LI); velvety to slightly floccose, thin, smooth, sporulation good; reverse olivaceous black (3) (LI) to black; no soluble pigment.

Potato Dextrose Agar—Colonies attaining 2.7 cm diam., growth good, andover green (XLVII), olive-gray to deep olive-gray (LI) with a pale olive-gray (LI) edge; velvety, , moderately raised, radiately wrinkled, sporulation good; reverse iron gray (LI) to black; no soluble pigment.

Glucose Agar—Colonies attaining 2.5 cm diam., growth moderate, light olive-gray, olive-gray to deep olive-gray (LI); velvety to slightly floccose, thin, smooth, sporulation good; reverse iron gray (LI) to black; no soluble pigment.

Oatmeal Agar—Colonies attaining 2.8 cm diam., growth poor to moderate, olive-gray, deep olive-gray to dark olive-gray (LI); velvety, thin, smooth, sporulation good; reverse same as surface; no soluble pigment.

Phytone. Yeast Extract Agar—Colonies attaining 3.0 cm diam., growth excellent, andover green (XLVII), light olive-gray, olive-gray to deep olive-gray (LI); velvety, highly raised, radiately wrinkled, sporulation good; reverse dark mouse gray (LD) to black; soluble pigment capucine yellow (III).

V-8 Juice Agar—Colonies attaining 2.8 cm diam., growth good, light olive-gray, olive-gray to deep olive-gray (LD; velvety to funiculose, thin to slightly raised, smooth, sporulation good; reverse dark olive-gray to olivaceous black (3) (LI); no soluble pigment.

Morphological Properties: The morphological properties were observed 14 days after incubation. On malt extract agar, the vegetative mycelium olive-gray to olive-brown, septate, branched, 1.5 to 4.0 mm diam; conidiophores macronematous, semi-macronematous, or micronematous, mononematous, septate, brown to olivaceous brown, smooth, monopodially or verticillately branched, 40–230 (–300)×2.0–3.5 mm, may branch up to four levels, with each level two to three subbranches, primary branches 20–40× 2.0–3.0 mm, secondary branches 15–30×2.0–2.5 mm, tertiary branches 10–12×2.0 mm; conidia olivaceous to olivaceous green, smooth or slightly roughened, one-celled, oval, elliptical, barrel-shaped to elongated, 3.0–7.0×2.0–4.0 mm, produced basipetally, maturing from top to bottom, arthrosporic in conidiogenesis; chlamydospores not produced. On potato dextrose agar, the morphological properties were similar to those on malt extract agar except that the conidiophores were generally shorter, and the conidia were shorter and narrower, measuring 3–6×1.6–3.0 mm.

Temperature Study: The growth was good at 20 and 28° C. but was none at 37, 45 and 50° C.

The culture FERM BP-5778 is characterized by the slow growth; the olive-gray to dark olive-gray colonies, the olivaceous black to black colony reverse; and the smooth to finely roughened, one-celled, olivaceous conidia which are arthrosporic in nature. It grows well at 20 and 28° C. but not between 37 and 50° C. It fits into the description of Oidiodendron griseum Robak in the general characteristics of morphologies and the cultural properties [Barron, G. L. 1962. New species and new records of Oidiodendron. Can. J. Bot. 40 (4): 589–607]. Minor differences were noted. Some conidiophores were taller and wider, and some conidia were barrel-shaped in addition to oval to elliptical and were slightly larger than those of the strains of *O. griseum*. As most species of Oidiodendron exhibit a wide range in conidiophore dimensions and conidial shapes, these differences are considered as minor variations. Thus, the strain CL-22682 is designated as a new strain of *Oidiodendron griseum* Robak.

In this invention, a mutant or recombinant form of *Oidiodendron griseum* FERM BP-5778 having the ability to produce the terpenoid compounds of formula (I) can be also used.

According to the present invention, the terpenoid compounds of formula (I) may be produced by aerobic fermentation of *Oidiodendron griseum* FERM BP-5778, or a mutant or recombinant form thereof, under conditions similar to those generally employed to produce bioactive compounds by fermentation.

FERM BP-5778, or a mutant or recombinant from thereof, is usually fermented under submerged aerobic conditions with agitation at a temperature of 20 to 40° C. for 5 to 14 days, which may be varied according to fermentation conditions. Cultivation of Oidiodendron griseum FERM BP-5778 to produce the terpenoid compounds of formula (I) preferably takes place in aqueous nutrient media at a temperature of 25 to 35° C. for 7 to 10 days. The pH of medium may be adjusted in the range from 4.0 to 9.0, preferably from 5.0 to 7.0.

Nutrient media useful for fermentation include a source of assimilable carbon such as sugars, starches and glycerol; a source of organic nitrogen such as casein, enzymatic digest of casein, soybean meal, cotton seed meal, peanut meal, wheat gluten, soy flour, meat extract and fish meal. A source of growth substances such as mineral salts, sodium chloride and calcium carbonate; and trace elements such as iron, magnesium, copper, zinc, cobalt and manganese may also be utilized with advantageous results. If excessive foaming is encountered during fermentation, antifoam agents such as polypropylene glycols or silicons may be added to the fermentation medium.

Aeration of the medium in fermenters for submerged growth is maintained at 3 to 200%, preferably at 50 to 150% volumes of sterile air per volume of the medium per minute. The rate of agitation depends on the type of agitator employed. A shake flask is usually run at 150 to 250 rpm whereas a fermenter is usually nm at 300 to 2,000 rpm. Aseptic conditions must, of course, be maintained through the transfer of the organism and throughout its growth.

The terpenoid lactone compounds thus produced may be isolated by standard techniques such as extraction and various chromatographic techniques.

The following terpenoid lactone compounds were isolated in a substantially pure form from the fermentation mixture: [5bS-(1aR*,5bβ,8aα,8bα,10aα,10bβ)]-5b,6,7,8,8a,8b,10a,10b-octahydro-2-hydroxy-5b, 8a-dimethyl-2H,4H,9H-furo[2',3',4':4,5]oxireno[2,3]naphtho [2,1-c]pyran-4,9-dione; [4S-(4aα,10bβ)]-1,2,3,4,4a,5,7,10b-octahydro-4-carboxy-4,10b-dimethyl-9H-naphtho[2,1-c]pyran-9-one; [2S-(1aR*,2α,5bβ,8aα,8bα,10aα,10bβ)]-5b,6,7,8,8a,8b,10a,10b-octahydro-2-methoxy-5b,8a-dimethyl-2H,4H,9H-furo[2',3',4':4,5]oxireno[2,3]naphtho[2,1-c]pyran-4,9-dione; [3aS-(3aα,5aα,7α,10bβ,10cα)]-1,2,3,3a,5a,7,10b,10c-octahydro-7-methoxy-3a,10b-dimethyl-4H,9H-furo[2',3',4':4,5] naphtho[2,1-c]pyran-4,9-dione; [3aS-(3aα,5aα,10bβ,10cα)]-1,2,3,3a,5a,7,10b,10c-octahydro-3a,10b-dimethyl-4H,9H-furo[2',3',4':4,5]naphtho[2,1-c]pyran-4,9-dione and [3aS-(3aα,5aα,7α,10bβ,10cα)]-1,2,3,3a,5a,7,10b,10c-octahydro-7-hydroxy-3a,10b-dimethyl4H,9H-furo[2',3', 4':4,5]naphtho[2,1-c]pyran-4,9-dione. The following fifteen compounds were synthesized from [2S-(1aR*,2α,5bβ,8aα,8bα,10aα,10bβ)]-5b,6,7,8,8a,8b,10a,10b-octahydro-2-methoxy-5b,8a-dimethyl-2H,4H,9H-furo[2',3',4':4,5]oxireno[2,3]naphtho[2,1-c]pyran-4,9-dione by chemical modification: [3aS-(3aα,5aα,6α,6aα,7α,10aα,10bβ,10cα)]-1,2,3,3a,5a,6,6a,7,10,10a,10b,10c-dodecahydro-6-hydroxy-7-methoxy-3a,10b-dimethyl4H,9H-furo[2',3',4':4,5] naphtho-[2,1-c]pyran-4,9-dione; [2S-(1aR*,2α,5aα, 5bβ, 8aα,8bα,10aα,10bβ)]-5,5a,5b,6,7,8,8a,8b,10a,10b-decahydro-2-methoxy-5b,8a-dimethyl-2H,4H,9H-furo[2',3',4':4,5]oxireno[2,3]naphtho[2,1-c]pyran-4,9-dione; [5bS-(1aR*,5bβ,8aα,8bα,10aα,10bβ)]-5b,6,7,8,8a,8b,10a,10b-octahydro-5b,8a-dimethyl-2H,4H,9H-furo[2',3',4':4,5]oxireno[2,3]naphtho[2,1-c]pyran-4,9-dione; [2aS-(1aR*, 2aβ,5aα,5bα,7aα,7bβ)]-2a,3,4,5,5a,5b,7a,7b-octahydro-1a-(hydroxymethyl)-2a,5a-dimethyl-1aH,6H-furo-[2',3',4':4,5] oxireno[2,3]-(E)-2-(1-naphthalenylidene)ethanol-6-one; [3aS-(3aα,5aα,6α,6aα,7α,10bβ,10cα)]-1,2,3,3a,5a,6,6a,7,10b,10c-decahydro-6-hydroxy-7-methoxy-3a,10b-dimethyl-4H,9H-furo[2',3',4':4,5]naphtho[2,1-c]pyran-4,9-dione; [5bS-(1aR*,5bβ,8aα,8bα,10aα,10bβ)]-5b,6,7,8,8a,8b,10a,10b-octahydro-2-methoxycarbonylmethyl-5b,8a-dimethyl-2H,4H,9H-furo[2',3',4':4,5]oxireno[2,3]naphtho[2,1-c]pyran-4,9-dione; [5bS-(1aR*,5bβ,8aα,8bα,10aα,10bβ)]-1a,2,5b,6,7,8,8a,8b,10a,10b-decahydro-3-(phenylmethyl)-5b,8a-dimethyl-3H,9H-furo[2',3',4':4,5]oxireno[2,3]naphtho[2,1-c]pyridine-4,9-dione; [5bS-(1aR*, 5bβ,8aα,8bα,10aα,10bβ)]-1a,2,5b,6,7,8,8a,8b,10a,10b-decahydro-3-propyl-5b,8a-dimethyl-3H,9H-furo[2',3',4':4,5]oxireno[2,3]naphtho[2,1-c]pyridine-4,9-dione; [5bS-(1aR*,5bβ,8aα,8bα,10aα,10bβ)]-1a,2,5b,6,7,8,8a,8b,10a,10b-decahydro-5b,8a-dimethyl-3H,9H-furo[2',3',4':4,5] oxireno[2,3]naphtho[2,1-c]pyridine4,9-dione; [2R-(1aR*, 2β,5bβ,8aα,8bα,10aα,10bβ)]-5b,6,7,8,8a,8b,10a,10b-octahydro-2-methoxy-5b,8a-dimethyl-2H,4H,9H-furo[2',3',4':4,5]oxireno[2,3]naphtho[2,1-c]pyran-4,9-dione [3aS-(3aα,5aα,6α,7α,10bβ,10cα)]-1,2,3,3 a,5a,6,6a,7,10b,10c-decahydro-6-hydroxy-6a-(2-ethoxycarbonyl-1-ethylthio)-7-methoxy-3a,10b-dimethyl-4H,9H-furo[2',3',4':4,5]naphtho [2,1-c]pyran-4,9-dione; [3aS-(3aα,5aα,6,10b,10cα)]-1,2,3,3a,5a,6,6a,7,10b,10c-decahydro-6-hydroxy-6a,7-di-(2-propylthio)-3a,10b-dimethyl-4H,9H-furo[2',3',4':4.5] naphtho[2,1-c]pyran-4,9-dione; [3aS-(3aα,5aα,6α,7α,10bβ,10cα)]-1,2,3,3a,5a,6,6a,7,10b,10c-decahydro-6-hydroxy-6a-(2-propylthio)-7-methoxy-3a,10b-dimethyl-4H,9H-furo[2',3',4':4,5]naphtho[2,1-c]pyran-4,9-dione; [2aS-(1aR*,2aβ,5aα,5bα,7aα,7bβ)]-2a,3,4,5,5a,5b,7a,7b-octahydro-1a-{2 -methoxycarbonyl-1-(E)-ethenyl}-2a,5a-dimethyl-1aH,6H-furo[2',3',4':4,5]oxireno[2,3]-(E)-(1-naphthalenylidene)acetic acid-6-one and butyl [2aS-(1aR*, 2aβ,5aα,5bα,7aα,7bβ]-2a,3,4,5,5a,5b,7b-octahydro-1a-(dibutoxymethyl)-2a,5a-dimethyl-1aH,6H-furo-[2',3',4':4,5]oxireno[2,3]-(E)-(1-naphthalenylidene)acetate-6-one. These compounds were identified by various spectroscopic techniques such as UV spectrophotometry, NMR and mass spectrometries, and the results are summarized in Table. The stereochemistry of these compounds (shown in Ex. 1 to 14) are believed to have the following structure.

Ex. 1

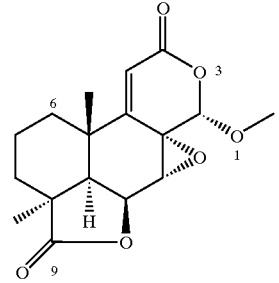

Ex. 1

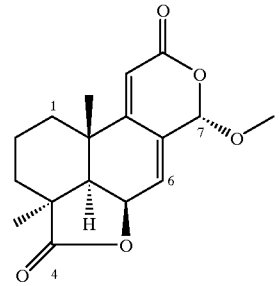

Ex. 1

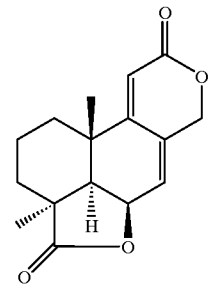

-continued
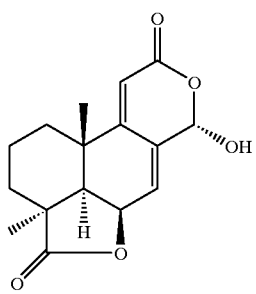
Ex. 1
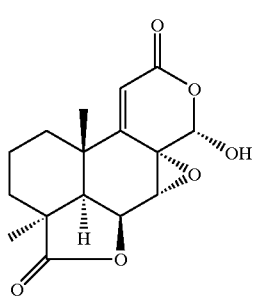
Ex. 1
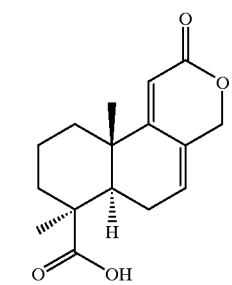
Ex. 1
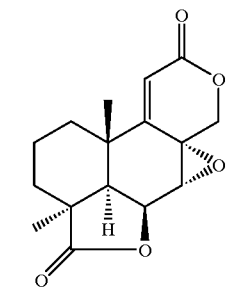
Ex. 2
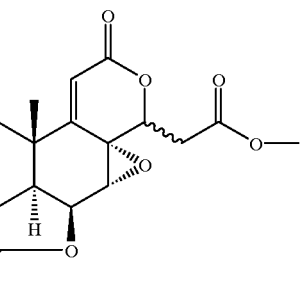
Ex. 3
-continued
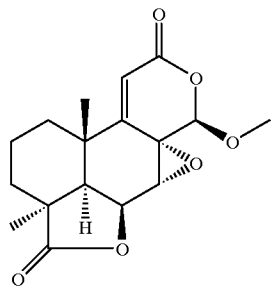
Ex. 4
Ex. 5
Ex. 5
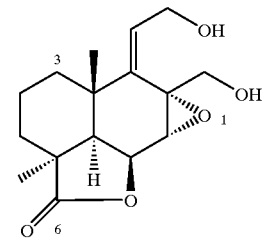
Ex. 6
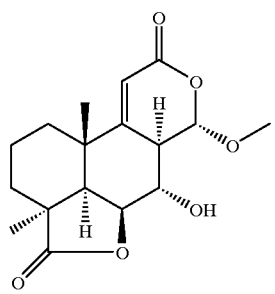
Ex. 7

Ex. 8
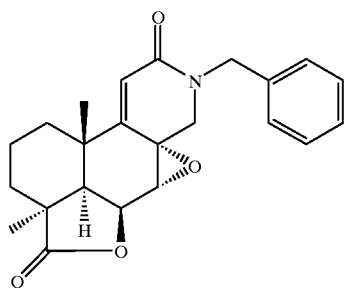

Ex. 9
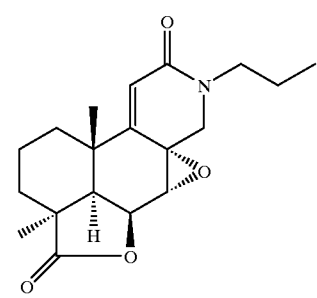

Ex. 10
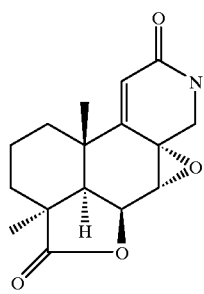

Ex. 11
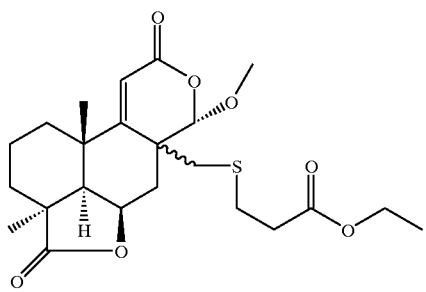

Ex. 12
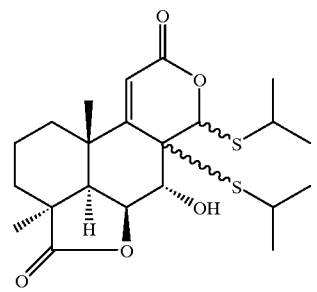

Ex. 12
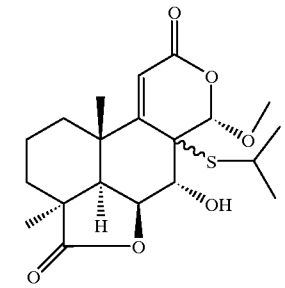

Ex. 13
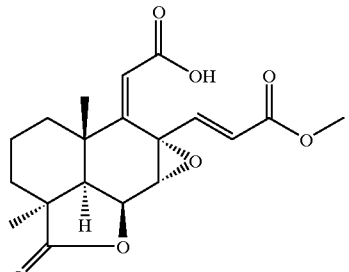

Ex. 14
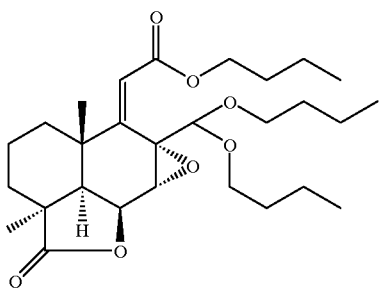

The compounds of this invention are useful in the treatment of IL-1 and TNF mediated diseases. The IL-1 and TNF production inhibitory activities of the terpenoid lactone compounds produced by the process of this invention were measured by the standard in vitro protocol described below:

TNF bioasy

Heparinised human whole blood diluted four-fold with RPMI was incubated with 10 mg/ml of Lipopolysaccharide (LPS) in the presence of various concentrations of samples at 37° C. in a humidified atmosphere containing 5% $CO_2$ for 4 h. TNF titer in human whole blood supematants was determined by cytotoxicity assay in highly TNF-sensitive L929 cells. $2.5 \times 10^4$ L929 cells in 100 ml of E-MEM containing 1% fetal calf serum and antibiotics were placed in wells of 96-well, flat-bottom, microplates and incubated overnight at 37° C. in a humidified atmosphere containing 5% $CO_2$. Within the wells containing L929 target cells, sequential ten-fold dilutions of human whole blood supernatants were made in the same medium containing 0.5 mg/ml of actinomycin D. After 18 h of incubation at 37° C. in a humidified atmosphere containing 5% $CO_2$, the plates were washed with 0.9% sterile saline and stained for 10 min with 0.4% crystal violet in 100% MeOH. The plates were rinsed again with distilled water and were air dried. 50 ml of 100% methanol were added to each well to elute the crystal violet, and the plates were read on a microplate reader (model 3550, BIO-RAD) at 595 nm. TNF inhibitory activity is calculated by the formula:

$$\text{Inhibition}(\%) = \left\{1 - \frac{[A595 \text{ Sample} - A595 \text{ Blank}]}{[A595 \text{ Control} - A595 \text{ Blank}]}\right\} \times 100$$

IL-1 bioassay

Human whole blood supernatants prepared by the same method as TNF bioassay were incubated with 10 mg/ml of LPS in the presence of various concentrations of samples at 37° C. in a humidified atmosphere containing 5% $CO_2$ for 4 h. IL-1 titer in human whole blood supernatants were analyzed for IL-1 production by specific ELISA. The plates were read on a microplate reader (model 3550, BIO-RAD) at 490 nm. IL-1 inhibitory activity is calculated by the formula:

$$\text{Inhibition}(\%) = \left\{1 - \frac{[A490 \text{ Sample} - A490 \text{ Blank}]}{[A490 \text{ Control} - A490 \text{ Blank}]}\right\} \times 100$$

A statistical program package Microsoft Excel for Macintosh was used to calculate $IC_{50}$ values. Most of the compounds prepared in the examples showed the $IC_{50}$ value in the range of 0.01 to 10.

Administration

In this invention, particularly useful compounds for the treatment of inflammation or the like are: [5bS-(1aR*,5bβ, 8aα,8bα,10aα, 10bβ)]-5b,6,7,8,8a,8b,10a, 10b-octahydro-2-hydroxy-5b,8a-dimethyl-2H,4H,9H-furo [2',3',4':4,5] oxireno[2,3]naphtho[2,1-c]pyran-4,9-dione; [5bS-(1aR*, 5bβ, 8aα,8bα, 10aα,10bβ)]-5b,6,7,8,8a,8b,10a, 10b-octahydro-5b,8-dimethyl-2H,4H,9H-furo[2',3',4':4,5] oxireno[2,3]naphtho[2,1 -c]pyran-4,9-dione; [5bS-(1aR*, 5bβ,8aα,8b,10aα,10bβ)]-5b,6,7,8,8a,8b,10a, 10b-octahydro-2-methoxycarbonylmethyl-5b,8a-dimethyl-2H, 4H,9H-furo [2',3',4':4,5]oxireno[2,3]naphtho[2,1-c]pyran-4, 9-dione; [2R-(1aR*, 2β,5bβ,8aα,8bα, 10aα, 10bβ)]-5b,6,7, 8,8a,8b,10a10b-octahydro-2-methoxy-5b,8a-dimethyl-2H, 4H,9H-furo[2',3',4':4,5]oxireno[2,3]naphtho[2,1-c]pyran-4, 9-dione; [3aS-(3aα,5aα, 6α, 7α,10bβ,10c α)]-1,2,3,3a,5a,6, 6a,7,10b,10c-decahydro-6-hydroxy-6a-(2-ethoxycarbonyl-1-ethylthio)-7-methoxy-3a, 10b-dimethyl4H,9H-furo[2',3', 4':4,5]naphtho[2,1-c]pyran-4,9-dione; [2aS-(1aR*,2aβ,5aα, 5bα,7aα,7bβ)]-2a,3,4,5, 5a,5b,7a,7b-octahydro-1a-{2-methoxycarbonyl-1-(E)-ethenyl}-2a,5a-dimethy-1aH,6H-furo[2',3',4':4,5]oxireno[2,3]-(E)-(1-naphthalenylidene) acetic acid-6-one; [2S-(1aR*, 2α,5bβ,8aα,8bα,10aα, 10bβ)]-5b,6,7,8,8a,8b,10a,10b-octahydro-2- methoxy-5b, 8a-dimethyl-2H,4H,9H-furo[2',3',4':4,5]oxireno[2,3] naphtho[2,1-c]pyran-4,9-dione; [3aS-(3aα,5aα,7α,10bβ, 10cα)]1,2,3,3a,5a,7,10b, 10c-octahydro-7-methoxy-3a,10b-dimethyl-4H,9H-furo[2',3',4':4,5]naphtho[2,1-c]pyran-4,9-dione; [3aS-(3aα,5aα, 10bβ,10cα)]-1,2,3,3a,5a,7,10b, 10c-octahydro-3a, 10b-dimethyl-4H,9H-furo[2',3',4':4,5] naphtho[2,1-c]pyran-4,9-dione and [3aS-(3aα,5aα,7α, 10bβ,10cα)]-1,2,3,3a,5a,7,10b, 10c-octahydro-7-hydroxy-3a,10b-dimethyl-4H,9H-furo[2',3',4':4,5]naphtho[2,1-c] pyran-4,9-dione. These compounds may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions comprising the terpenoid compounds and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calciun phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often usefull for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredients therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the terpenoid compounds in sesame or peanut oil, aqueous propylene glycol, or in sterile aqueous solution may be employed. Such aqueous solutions should be suitable buffered if necessary and the liquid diluent first rendered isotonic with sufficient saline or glucose. These particular aqueous solutions are especially suitable for intravenous, intramuscular, subcutaneous and intraperitioneal administration. In this connection, the sterile aqueous media employed are all readily available by standard techniques known to those skilled in the art.

Additionally, the terpenoid compounds may be administered topically when treating conditions of the skin and this may be done by way of creams, jellies, gels, pastes, and ointments, in accordance with standard pharmaceutical practice.

In general, the terpenoid compounds are present in the above dosage fonns at concentration levels ranging 5 to 70% by weight, preferably 10 to 50% by weight.

In general, a therapeutically effective daily dose for the active compound will range from 0.01 to 100 mglks, generally from about 1 to about 5 mg/kg As is generally known, the effective dosage for the active compound depends on the intended route of administration and other factors such as age and weight of the patient, as generally known to a physician. The dosage also depends on the illness to be treated.

EXAMPLES

The present invention is illustrated by the following examples. However, it should be understood that the invention is not limited to the specific details of these examples. Spectral and physico-chemical data were obtained by the following insents: UV, JASCO Ubest-30; NMR, JEOL JNM-GX270 updated with a LSI-11/73 host computer, TH-5 tunable probe and version 1.6 software; and LRFAB- and HRFAB-MS, JEOL JMS-700 Mstation. All NMR spectra were measured in $CD_3OD$ unless otherwise indicated and peak positions are expressed in parts per million (ppm) based on the internal standard of the $CH_3OH$ peak at 3.35 ppm for $^1H$ NMR and 49.0 ppm. for $^{13}C$ NMR. The peak shapes are denoted as follows: s (singlet), d (doublet), t (trplet), q (quartet), m (multiplet) and br (broad). All FAB-MS spectra were measured using glycerol-matrix.

Example One

Fermentation of *Oidiodendron griseum* FERM EP-5778

One hundred ml of Medium-1 (potato dextrose broth 2.4%, yeast extract 0.5% and agar 0.1%) in a 500-ml flask was inoculated with a vegetative cell suspension from a slant culture of *Oidiodendron griseum* FERM BP-5778. The flask was shaken at 26° C. for 4 days on a rotary shaker with 7-cm throw at 210 rpm, to obtain a seed culture.

Four 500-ml flasks containing Medium-1 (1.50 ml) was inoculated with 5 ml of the first seed culture. The flask was shaken at 26° C. for 3 days on a rotary shaker, to obtain second seed cultures.

The four second seed cultures were used to inoculate four 6-1 fermentation vessel containing 31 of sterile medium (Medium-2: Medium-2: lucose 3%, malt extract 15%, yeast extract 0.5%, $MgSO_4 \cdot 7H_2O$ 0.05% and $KH_2PO_4$ 0.1%, pH 6.0). Aeration was carried out at 26° C. for 7 days with 1,700 rpm at 31 per min.

Extraction and Isolation

The fermentation broth (41) was filtered after the addition of 41 of ethanol. The filtrate was concentrated to aqueous solution (11). Then it was extracted 3 times with each of 11 of ethyl acetate. The extract was dried over anhydrous $Na_2SO_4$ and evaporated. The extract (2.8 g) was crystallized and solved with acetonirile. The solution was applied to a column sold under the trade name YMC-pack ODS AM-343 (20×250 mm, Yamamura) and eluted with methanol in water (40:60) for 40 min at flow rate of 10 m/min. Detection was made by UV absorbance at 220 nm. The eluted peaks were collected to yield the [2S-(1aR*,2α,5bβ,8aα,8bα,10aα, 10bβ)]-5b,6,7,8,8a,8b,10a,10b-octahydro-2-methoxy-5b, 8a-dimethyl-2H,4H,9H-furo [2',3',4':4,5]oxireno[2,3] naphtho[2,1-c]pyran-4,9-dione (101.8 mg), [3aS-(3aα,5aα, 7α,10Obβ,10cα)]-1,2,3,3a,5a,7,10b,10c-octahydro-7-methocy-3a,10b-dimethyl-4H,9H-furo[2',3',4':4,5]naphtho [2,1-c]pyran4,9-dione (0.8 mg) and [3aS-(3aα,5aα,10bβ, 10cα)]-1,2,3,3a,5a,7,10b,10c-octahydro-3a, 10b-dimethyl-4H,9H-furo[2',3',4':4,5]naphtho[2,1-c]pyran-4,9-dione (2.4 mg). The supernatant removed crystal was applied to a column sold under the trade name of YMC-pack ODS AM-343 (20×250 mm, Yamamura) and eluted with acetonirile in 0.1% TFA (40:60) for 40 min at flow rate of 8 ml/min. Detection was made by UV absorbance at 220 nm. The eluted peaks were collected to yield the [3aS-(3aα,5aα,7α, 10bβ,10cα)]-1,2,3,3a,5a,7,10b, 10c-octahydro-7-hydroxy-3a, 10b-dimethyl-4H,9H-furo[2',3',4':4,5]naphtho[2, 1-c] pyran-4,9-dione (20.8 mg), [5bS-(1aR* ,5bβ,8aα,8bα,10aα, 10bβ)]-5b,6,7,8,8a,8b,10a,10b-octahydro-2-hydroxy-5b,8a-dimethyl-2H,4H,9H-furo [2',3',4':4,5]oxireno[2,3]naphtho [2,1-c]pyran-4,9-dione (17.6 mg) and [4S-(4aα,10bβ)]-1,2, 3,4,4a,5,7,10b-octahydro-4-carboxy-4,10b-dimethyl-9H-naphtho[2,1-c]pyran-9-one (13.7 mg).

HPLC Analysis

Analytical HPLC of the terpeneid lactone compounds, [2S-(1aR*,2α,5bβ,8aα,8bα,10aα,10bβ)]-5b,6,7,8,8a,8b, 10a, 10b-octahydro-2-methoxy-5b,8a-dimethyl-2H,4H,9H-furo[2',3',4':4,5]oxireno[2,3]naphtho[2,1-c]pyran-4,9-dione; [3aS-(3aα,5aα,7α,10bβ,10cα)]-1,2,3a,5a,7,10b 10c-octahydro-7-methoxy-3a,10b-dimethyl-4H,9H-furo[2',3', 4':4,5]naphtho[2,1-c]pyran-4,9-dione and [3aS-(3aα,5aα, 10bβ,10cα)]-1,2,3,3a,7,10b, 10c-octahydro-3a, 10b-dimethyl-4H,9H-furo[2',3',4':4,5]naphtho[2,1-c]pyran-4,9-dione was performed using a column sold under the tradename of YMC-pack ODS AM-312 (6.0×150 mm, Yamamura) and eluted with acetonirile in water (45:55) at a flow rate of 0.8 ml/min. The retention times of [2S-(1aR*, 2α,5bβ,8aα,8bα,10aα,10bβ)-5b,6,7,8,8a,8b,10a,10b-octahydro-2-methoxy-5b,8a-dimethyl-2H,4H,9H-furo[2',3', 4':4,5]oxireno[2,3]naphtho[2,1-c]pyran-4,9-dione; [3aS-(3aα,5aα,7α,10bβ,10cα)]-1,2,3,3a,5a,7,10b, 10c-octahydro-7-methoxy-3a,10b-dimethyl-4H,9H-furo[2',3', 4':4,5]naphthol[2,1-c]pyran-4,9-dione and [3aS-(3aα,5aα, 10bβ,10cα)]-1,2,3,3a,5a,7,10b, 10c-octahydro-3a,10b-dimethyl-4H,9H-furo[2',3',4':4,5]naphtho[2,1-c]pyran-4,9-dione were 9.8, 8.3 and 11.4 min, respectively. Also, analytical HPLC of the terpenoid lactone compounds, [3aS-(3aα,5aα,7α,10bβ,10cα))-1,2,3,3a,5a,7,10b,10c-octahydro-7-hydroxy-3a, 10b-dimethyl-4H,9H-furo[2',3',4':4,5] naphtho[2,1-c]pyran-4,9-dione; [5bS-(1aR*,5bβ,8aα,8bα, 10aα,10bβ)-5b,6,7,8,8a,8b,10a,10b-octahydro-2-hydroxy-5b,8a-dimethyl-2H,4H,9H-furo[2',3',4':4,5]oxireno[2,3] naphtho[2,1-c]pyran-4,9-dione and [4S-(4aα,10bβ)]-1,2,3, 4,4a,5,7,10b-octahydro-4-carboxy-4,10b-dimethyl-9H-naphtho(2,1-c]pyran-9-one was performed using a column sold under the trade name of YMC-pack ODS AM-312 (4.6×50 mm, Yamamura) and eluted with acetonitile in water (40:60) at a flow rate of 0.8 ml/min. The retention times of [3aS-(3aα,5aα,7α,10bβ,10cα)]-1,2,3,3a,5a,7,10b, 10c-octahydro-7-hydroxy-3a,10b-dimethyl-4H,9H-furo(2',3', 4':4,5]naphtho[2,1-c]pyran-4,9-dione; [5bS-(1aR*,5bβ,8aα, 8bα,10aα,10bβ)]-5b,6,7,8,8a,8b,10a,10b-octahydro-2-hydroxy-5b,8a-dimethyl-2H,4H,9H-furo [2',3',4':4,5] oxireno[2,3]naphtho[2,1-c]pyran-4,9-dione and [4S-(4aα, 10bβ)]-1,2,3,4,4a,5,7,10b-octahydro-4-carboxy-4,10b-dimethyl-9H-naphtho [2,1-c]pyran-9-one were 4.3, 5.8 and 6.3 min, respectively.

Characterization

The physico-chemical properties of [5bS-(1aR*,5bβ,8aα, 8bα,10aα,10bβ)]-5b,6,7,8,8a,8b,10a,10b-octahydro-2-hydroxy-5b,8a-dimethyl-2H,4H,9H-furo[2',3',4':4,5] oxireno[2,3]naphtho[2,1-c]pyran-4,9-dione and [4S-(4aα, 10bβ)]-1,2,3,4,4a,5,7,10b-octahydro-4-carboxy-4,10b-dimethyl-9H-naphtho[2,1-c]pyran-9-one are as follows:
[5bS-(1aR*,5bβ,8aα,8bα,10aα,10bβ)]-5b,6,7,8,8a,8b,10a, 10b-octahydro-2-hydroxy-5b,8a-dimethyl-2H,4H,9H-furo [2',3',4':4,5]oxireno[2,3]naphtho[2,1-c]pyran-4,9-dione: white amorphous powder; molecular formula $C_{16}H_{18}O_6$, LRFAB-MS m/z 305 [M-H]; HRFAB-MS m/z 305.104 (calcd. for $C_{16}H_{17}O_6$, 305.099); $[a]_D^{23}$–21.0_(c 0.3 1, MeOH); UV $1_{max}$ (MeOH) nm 208, 225; IR $g_{max}$ (KBr) $cm^{-1}$ 3350, 2935, 1770, 1694, 1198, 1091, 1038, 974, 924; $^1$H-NMR ($CD_3OD$) d 6.03 (1H, s), 5.06 (1H, dd, J 4.3, 1.1 Hz), 4.01 (1H, d, J=1.1 Hz), 2.15 (1H, m), 1.92 (1H, d, J=4.3 Hz), 1.73 (3H, m), 1.53 (2H, m), 1.27 (3H, s), 1.10 (3H, m); $^{13}$C-NMR d 183.5 (s), 166.1 (s), 158.7 (s), 119.1 (d), 74.6 (d), 59.5 (s), 55.8 (d), 46.2 (d), 44.1 (s), 37.8 (s), 31.4 (t), 30.4 (t), 25.2 (q), 25.2 (q), 19.4 (t).
[4S-(4aα,10bβ)]-1,2,3,4,4a,5,7, 10b-octahydro-4-carboxy-4,10b-dimethyl-9H-naphtho[2,1-c]pyran-9-one: white amorphous powder; molecular formula $C_{16}H_{20}O_5$; LRFAB-MS m/z 275 [M-H][31] ; HRFAB-MS m/z 275.131 (calcd. for $C_{16}H_{18}O_4$, 275.122); $[a]_D^{24}$–54.8_(c 0.04, MeOH); UV $1_{max}$ (MeOH) nm 207, 226; IR $g_{max}$ (KBr) $cm^{-1}$ 3435, 2930, 1701, 1652, 1021, 1051, 959; $^1$H-NMR ($CDCl_3$) d 6.09 (1H, brs), 5.71 (1H, s), 4.85 (1H, brd, J=13.2 Hz), 4.76 (1H, brd, J=13.2 Hz), 2.91 (1H, m), 2.53 (1H, m), 2.23 (1H, d, J=13.5 Hz), 1.95 (2H, m), 1.64 (2H, dd, J=11.3, 4.3 Hz), 1.45 (1H, m), 1.27 (3H, s), 1.09 (1H, m), 1.00 (3H, s); $^{13}$C-NMR d 182.5 (s), 165.8 (s), 162.9 (s), 131.1 (d), 125.0 (s), 109.8 (d),69.6 (t), 48.9 (d), 43.9 (s), 37.5 (s), 37.4 (t), 35.8 (t), 28.2 (q), 24.7 (t), 19.3 (q), 19.2 (t).

Example Two

Preparation of [5bS-(1aR*,5bβ,8aα,8bα,10aα, 10bβ)-5b,6,7,8a,8b, 10a,10b-octahydro-5b,8a-dimethy1-2H,4H,9H-furo [2', 3',4':4,5]oxireno[2,3]naphtho[2,1-c]pyran-4,9-dione A mixture of [2S-(1aR*,2α,5bβ,8aα,8bα,10aα,10bβ)]-5b,6,7,8,8a,8b,10a,10b-octahydro-2-methoxy-5b,8a-dimethyl-2H,4H,9H-furo [2',3',4':4,5]oxireno[2,3]naphtho[2,1-c]pyran4,9-dione (50.0 mg, 6.41 mmol) and AcOH—H$_2$O—THF (3:1:1, 10.0 ml) was stirred and heated at a bath temperature of 70° C. for 75 hours. The reaction mixture was then concentrated in vacuo at a bath temperature below 70° C. to give crude [5bS-(1aR*, 5bβ,8aα,8bα,10aα,10bβ)]-5b, 6,7,8,a,8b,10a,10b-octahydro-2-hydroxy-5b,8a-dimethyl-2H,4H,9H-furo[2',3',4':4,5]oxireno2,3]naphtho[2,1-c] pyran-4,9-dione as a colorless solid: MS (70 eV) mz 307 (M$^+$+1, 0.76%) 306 (M$^+$, 0.61%). This was dissolved in THF-MeOH (4:1, 2.50 ml). The resultant solution was ice-cooled, and then NaBH$_4$ (0.21 g, 3.21 mmol) was added portionewise. After the stirring was continued under the same cooling conditions for 10 minutes, 1M HCl aq. solution was added until the reaction mixture became acidic (litmus red). The mixture was saturated with NaCl, and then extracted with EtOAc (×7) thoroughly. The combined EtOAc extracts were washed with sat. NaCl aq. solution (×1), dried (MgSO$_4$), and concentrated in vacuo to give a mixture of [5bS-(1aR*,5bβ,8aα,8bα,10aα,10bβ)]-5b,6,7,8, 8a,8b,10a,10b-octahydro-5b,8adimethyl-2H,4H,9H-furo(2', 3',4':4,5]oxireno[2,3]naphtho[2,1-c]pyran-4,9-dione and its seco acid in a ratio of 1:2.7 in favor of the latter, as shown by $^1$H-NMR. To the crude product thus obtained was added dry PhMe (2.0 ml), and the resultant mixture was stirred and heated at reflux. overnight to drive the lactonization to completion. The yellow reaction mixture was concentrated in vacuo, and the solid residue was purified by preparative TLC [Merck Kieselgel 60, Art 5744, 0.5mm thick, ×2; development, n-hexane-EtOAc (1:1), ×2; efution, CH$_2$Cl$_2$—MeOH (10:1)] to give [5bS-(1aR*,5bβ,8aα,8bα,10aα, 10bβ)]-5b,6,7,8,8a, 8b,10a,10b-octahydro-5b,8a-dimethyl-2H,4H,9H-furo [2',3',4':4,5]oxireno[2,3]naphtho[2,1-c] pyran-4,9-dione (36.0 mg, 79.5%) as a white solid: $^1$H-NMR (270 MHz) d (CDCl$_3$) 6.02 (1H, s), 4.98 (1H ,dd, J=4.4, 1.5 Hz), 4.70 (1H, d, J=12.3 Hz), 4.30 (1H, d, J=12.3 Hz), 3.89 (1H, d, J=1.5 Hz), 2.23 (1H, ddd, J=15.0, 4.9, 4.9 Hz)), 1.87 (1H, d, J=4.4 Hz), .1.85~1.63 (3H, m), 1.63~1.43.(2H, m), 1.29 (3H, s), 1.15 (3H, s) ppm; MS (70 eV) m/z 291 (M$^+$+1, 4.5% ), 290 (M$^+$3.8%), 219 (62.1%), 202 (43.2%), 145 (66,7%), 91 (100%).

Example Three

Preparation of [5bS-(1aR*,5bβ,8aα,8bα,10aα, 10bβ)]-5b,6,7,8,8a,8b10a,10b-octahydro-2-metboxycarbonylmethyl-5b,8a-dimethyl-2H,4H,9H-furo[2',3',4':4,5]oxireno[2,3]naphtho[2,1-c]pyran-4,9-dione Under an atmosphere of N$_2$, dry THF (3.0 ml) was added to a mixture of Ph$_3$P═CHCO$_2$Me (98.2 mg, 0.29 mmol) and [5bS-(1aR* 5bβ,8aβ,8bα,10aα,10bβ)]-5b,6,7,8,8a,8b,10a, 10b-octahydro-2-hydroxy-5b,8a-dimethyl-2H,4H,9H-furo [2',3',4':4,5]oxireno[2,3]naphtho[2,1-c]pyran-4,9-dione (30.0 mg, 0.10 mmol; prepared as described in Example Two). The resultant homogeneous mixture was stirred and heated at reflux for two hours. The mixture was then concentrated in vacuo. The solid residue was subjected to preparative TLC [Merck Kieselgel 60, Art 5,744,.0.5 mm, ×3; development, n-hexane-EtOAc (2:3)]. The fraction of the second fastest mobility was separated, and eluted with CH$_2$Cl$_2$—MeOH (10:1) to give [5bS-(1aR*, 5bβ,8aα,8bα, 10aα,10bβ)]-5b,6,7,8,8a,8b,10a,10b,-octahydro-2-methoxycarbonylmethyl-5b,8a-dimethyl-2H,4H,9H-furo [2',3',4':4,5]oxireno[2,3]naphtho[2,1-c]pyran-4,9-dione (2.0 mg, 5.5%): $^1$H-NMR (270 MHz) d (CDCl$_3$) 6.04 and 6.02 (total 1H, each s), 5.17 and 4.70 (total 1H, each t, J=6.4 and 6.4 Hz), 4.96 and 4.93 (total 1H, each d, J=4.0 and 4.4 Hz), 4.04 (1H, br. s), 3.75 and 3.74 (total 3H, each s), 2.87 and 2.69 (total 1H, each dd, J=16.4 and 6.4 Hz), 2.40~2.16 (2H, m), 1.86 and 1.84 (total 1H, each d, J=4.4 and 4.0 Hz), 1.85~1.40 (4H, m), 1.29 and 1.25 (total 3H, each s), 1.17 and 1.09 (total 3H, each s) ppm; MS (70 eV) m/z 362 (M$^+$+1, 3.8%), 331 (13.6%), 330 (27.2%), 303 (16.6%), 291 (100%). Judging from the $^1$H-NMR spectrum, the [5bS-(1aR*,5bβ,8aα,8bα,10aα,10bβ)]-5b,6,7,8,8a,8b,10a, 10b-octahydro-2-methoxycarbonylmethyl-5b,8a-dimethyl-2H, 4H,9H-furo[2',3',4':4,5]oxireno[2,3]naphtho[2,1-c]pyran-4, 9-dione thus obtained was an almost (1:1) epimeric mixture at the newly created stereogenic center.

Example Four

Preparation of [2R-(1aR*,2β,5bβ,8aα,88α,10aα, 10bβ)]-5b,6,7,8,8a,8b,10a,10b-octahydro-2-methoxy-5b,8a-dimethyl-2H,4H,9H-furo[2',3',4':4,5] oxireno[2,3]naphtho[2,1-c]pyran-4,9-dione A solution of [2S-(1aR*,2α,5bβ,8aα,8bα,10aα,10bβ)]-5b,6,7,8,8a,8b,10a,10b-octahydro-2-methoxy-5b,8a-dimethyl-2H,4H,9H-furo[2',3',4':4,5]oxireno[2,3]naphtho [2,1-c]pyran-4,9-dione (15.0 mg, 0.047 mmol) and a bit of PPTS in CF$_3$CH$_2$OH (3.0 ml) was stirred at room tempertur overnight. The stirring was further continued with heating at a gentle reflux for three nights. After cooling, the reaction mixture was partitioned between EtOAc and H$_2$O. The EtOAc layer was separated, washed with H$_2$O (×2), sat. NAHCO$_3$ aq. solution (×1), dried (MgSO$_3$), and concentrated in vacuo to give a solid residue (10.2 mg). This was purified by preparative TLC [Merck Kieselgel 60, Art 1.05744, 0.5 mm, ×1; development, n-hexane-EtOAc (3:2)]. The fraction less polar than [2S-(1aR*,2α,5bβ,8aα,8bα, 10aα,10bβ)]-5b,6,7,8,8a,8b,10a,10b-octahydro-2-methoxy-5b,8a-dimethyl-2H,4H,9H-furo[2',3',4':4,5]oxireno[2,3] naphtho[2,1-c]pyran-4,9-dione was separated, and eluted with CH$_2$Cl$_2$—MeOH (10:1) to give [2R-(1aR*,2β,5bα, 8aα,8bα,10aα,10bβ)]-5b,6,7,8,8a,8b, 10a,10b-octahydro-2-methoxy-5b,8a-dimethyl-2H,4H,9H-furo[2',3',4':4,5] oxireno[2,3]naphtho[2,1-c]pyran-4,9-dione (2.9 mg, 19.3%): $^1$H-NMR (270 MHz) d (CDCl$_3$) 6.00 (1H, s), 5.30 (1H, s), 4.95 (1H, dd, J=4.6, 1.1 Hz), 3.93 (1H, d, J=1.1 Hz), 3.56 (3H, s), 2.31~2.18 (1H, m), 1.85 (1H, d, J=4.6 Hz), 1.84~1.44 (5H, m), 1.29 (3H, s), 1.11 (3H, s) ppm.

Example Five

Preparation of [3aS-(3aα,5aα,6α,6aα,7α,10aα, 10bβ,10cα)]-1,2,3,3a,5a,6,6a,7,10,10a,10b,10c-dodecahydro-6-hydroxy-7-methoxy-3a,10b-dimethyl-4H,9H-furo[2',3',4':4,5]naphtho-[2,1-c] pyran-4,9-dione and [2S-(1aR*,2α,5aα,5bβ,8aα, 8bα,10aα,10bβ)]-5,5a,5b,6,7,8,8a,8b,10a,10b-decahydro-2-methoxy-5b,8a-dimethyl-2H,4H,9H-furo[2',3', 4':4,5]oxireno[2,3]naphtho[2,1-c]pyran-4, 9-dione A heterogeneous mixture of [2S-(1aR*, 2α,5bβ,8aα,8bα, 10aα,10bβ)]-5b,6,7,8,8a,8b,10a,10b-octahydro-2-methoxy- 5b,8a-dimethyl-2H,4H,9H-furo[2',3',4':4,5]oxireno[2,3] naphtho[2,1-c]pyran-4,9-dione (80 mg, 0.250 mmol), $PtO_2$ (18 mg), and EtOH—THF (4:1, 10.0 ml) was stirred under an atmosphere of hydrogen (baloon) at room temperature overnight. The catalyst was filtered off by the.aid of Celite, and the filter cake was washed with THF (×3). The combined filtrate and washings were concentrated in vacuo to give a colorless foam (76.8 mg). This was subjected to preparative TLC [Merck Kieselgel 60, Art 5,744, 0.5 mm thick, ×2; development: n-hexane—AcOEt (2:3); elution: AcOEt] to give [3aS-(3aα,5aα,6α,6aα,7α,10aα,10bβ, 10cα)]-1,2,3,3a,5a6,6a,7,10, 10a,10b,10c-dodecahydro-6-hydroxy-7-methoxy-3a, 10b-dimethyl-4H,9H-furo[2',3', 4':4,5]naphtho-[2,1-c]pyran-4,9-dione as a more polar product (19.8 mg, 24.4%): $^1$H-NMR (270 MHz) d($CDCl_3$) 5.41 (d, J=2.2 Hz, 1H), 4.72 (dd, J=5.6, 5.6 Hz, 1H), 4.49~4.33 (m, 1H), 3.95 (d, J=4.0 Hz, 1H), 3.55 (s, 3H), 2.81 (dd, J=15.8, 8.2 Hz, 1H), 2.38 (dd, J=15.8, 3.1 Hz, 1H), 2.30~2.07 (m, 3H), 1.79 (d, J=5.6 Hz, 1H), 1.72~1.48 (m, 3H), 1.48~1.39 (m, 1H), 1.29 (s, 3H), 1.09~0.93 (m, 1H), 0.79 (s, 3H) ppm; MS (70 eV) m/z 324 (0.23%, $M^+$), 309 (0.68%, $M^+$—$CH_3$), 306 (0.15%, $M^+$—$H_2O$), 293 (3.8%, $M^+$—$OCH_3$), 264 (22.7%, $M^+$—$CH_3CO_2H$), 222 (32.3%), 109 (50%), 87 (100%); and [2S-(1aR*, 2α,5aα,5bβ,8aα, 8bα,10aα,10bβ)]-5,5a,5b,6,7,8,8a,8b, 10a,10b-decahydro-2-methoxy-5b,8a-dimethyl-2H,4H,9H-furo [2',3',4':4,5] oxireno[2,3]naphtho[2,1-c]pyran-4,9-dione as a less polar product (40.9 mg, 50.7%): $^1$H-NMR (270 MHz) d($CDCl_3$) 4.91 (d, J=4.8 Hz, 1H), 4.71 (s, 1H), 3.66 (s, 1H), 3.58 (s, 3H), 3.05 (dd, J=16.5, 8.6 Hz, 1H), 2.60 (dd, J=16.5, 2.6 Hz, 1H), 2.25~2.07 (m, 1H), 1.94 (dd, J=8.6, 2.6 Hz, 1H), 1.65 (d, J=4.8 Hz, 1H), 1.73~1.36 (m, 4H), 1.28 (s, 3H), 1.15~1.00 (m, 1H), 0.87 (s., 3H) ppm; MS (70 eV) m/z 322 (0.16%, $M^+$), 309 (0.68%, $M^+$—$CH_3$), 291 (6.1%, $M^{30}$—$OCH_3$), 262 (40.2%, $M^+$—$CH_3CO_2H$), 203 (35.6%), 175 (60.6%), 147 (36.4%), 109 (100%).

Example Six

Preparation of [2aS-(1aR*,2aβ,5aα,5bα,7aα,7bβ)]-2a,3,4,5,5a 5b,7a,7b-octahydro-1a-(hydroxymethyl)-2a,5a-dimethyl-1aH,6H-furo-[2',3',4':4,5]oxireno[2, 3]-(E)-2-(1-naphthalenylidene)ethanol-6-one To a stirred and dry ice—acetone—cooled solution of [2S-(1aR*,2α,5bβ,8aα,8bα,10aα,10bβ) ]-5b,6,7,8,8a,8b, 10a,10b-octahydro-2-methoxy-5b,8a-dimethyl-2H,4H,9H-furo[2',3',4':4,5]oxireno[2,3]naphtho[2,1-c]pyran-4,9-dione (50.0 mg, 0.156mmol) in dry THF (2.5ml) was added a 1.0M solution of $LiAlH_4$ in $Et_2O$ (0.090 ml, 0.090 mmol) dropwise under an atmosphere of nitrogen. After stirring under the same cooling conditions for an hour, the cooling bath was replaced with an ice bath. The stirring was then continued further for an hour. The reaction was quenched with $Na_2SO_4.10H_2O$. The mixture was filtered through a short pad of Celite, and the filter cake was washed with THF throughly. The combined filtrate and washings were dried ($MgSO_4$) and concentrated in vacuo to give a colorless syrup (42.5 mg). This was purified by preparative TLC [Merck Kieselgel 60, Art 5,744, 0.5mm thick, ×2; development: n-hexane—ACOEt (2:3)×2; elution: $CH_2Cl_2$—MeOH (10:1), 110 ml] to give [2aS-(1aR*, 2aβ,5aα,5bα,7aα,7bβ)]-2a,3,4,5,5a,5b,7a,7b-octahydro-1a-(hydroxymethyl)-2a,5a-dimethyl-1aH,6H-furo-[2',3',4':4,5]oxireno[2,3]-(E)-2-(1-naphthalenylidene)ethanol-6-one as a colorless syrup (21.6 mg, 47.1%): $^1$H-NMR (270 MHz) d($CDCl_3$) 5.71 (t, J=7.1 Hz, 1H), 4.88 (d, J=4.4 Hz, 1H), 4.41~4.24 (m, 2H), 3.99 (d, J=13.2 Hz, 1H), 3.82 (d, J=13.2, 6.6 Hz, 1H), 3.76 (s, 3H), 2.36~2.19 (m, 2H), 1.95 (br.s, 1H), 1.75~1.57 (m, 3H), 1.57 1.47 (m, 1H), 1.47~1.23 (m, 2H), 1.23 (s, 3H), 1.03 (s, 3H) ppm; MS (70 eV) m/z 294 (0.5%, $M^+$), 276 (7.9%, $M^+$—$H_2O$), 263 (26.4%), 151 (58.1%), 133 (59.2%), 109 (100%).

Example Seven

Preparation of [3aS-(3aα,5aα,6α,6aα,7α,10bβ, 10cα)]-1,2,3,3a,5a,6,6a,7,10b,10c-decahydro-6-hydroxy-7-methoxy-3a,10b-dimethyl-4H,9H-furo[2', 3',4':4,5]naphtho[2,1-c]pyran4,9-dione A heterogeneous mixture of [2S-(1aR* ,2α,5bβ,8aα,8bα, 10aα,10bβ)]-5b,6,7,8,8a,8b,10a,10b-octahydro-2-methoxy-5b,8a-dimethyl-2H,4H,9H-furo[2',3',4':4,5]oxireno[2,3] naphtho[2,1-c]pyran-4,9-dione (40.0 mg, 0.125 mmol), 10% Pd-C (12.6 mg), and EtOH—THF (2:3) was stirred under an atmosphere of $H_2$ (baloon) at room temperature for 30 minutes. The catalyst was filtered off by the aid of Celite, and the filter cake was washed with THF. The combined filtrate and washings were concentrated in vacuo to give a pale yellow solid (37.3 mg). This was purified by preparative TLC [Merck Kieselgel 60, Art 5,744, 0.5 mm thick, ×2; development: $CH_2Cl_2$—MeOH (10:1), 110 ml] to give [3aS-(3aα,5aα,6α,6aα,7α, 10bβ,10cα)]-1,2,3,3a,5a,6,6a,7,10b, 10c-decahydro-6-hydroxy-7-methoxy-3a,10b-dimethyl4H, 9H-furo[2',3',4':4,5]naphtho[2,1-c]pyran-4,9-dione as a colorless solid (11.2 mg, 27.8%): $^1$H-NMR (270 MHz) d($CDCl_3$) 5.86 (d, J=2.9 Hz, 1H), 5.19 (d, J=10.2 Hz, 1H), 4.78 (dd, J=5.3, 4.4 Hz, 1H), 4.44 (dd, J=10.2, 4.4 Hz, 1H), 3.90 (s, 1H), 3.72 (s, 3H), 2.72 (ddd, J=10.2, 10.2, 2.9 Hz, 1H), 2.44 (ddd, J=14.6, 5.5, 5.5 Hz, 1H), 1.95 (d, J=5.3 Hz, 1H), 1.90~1.77 (m, 1H), 1.77~1.65 (m, 1H), 1.65~1.55 (m, 1H), 1.54~1.37 (m, 2H), 1.32 (s, 3H), 1.07 (s, 3H) ppm; MS (70 eV) m/z 323 (0.6%, $M^+$+1), 321 (0.8%, $M^+$−1), 291 (6.8%), 290 (8.0%), 263 (81.8%), 262 (99.0%), 163 (64.4%), 150 (88.6%), 137 (98.0%), 109 (100%).

Example Eight

Preparation of [5bS-(1aR*,5bβ,8aα,8bα,10aα, 10bβ)]-1a,2,5b,6,7,8,8a,8b,10a,10b-decahydro-3-(phenylmethyl)-5b,8a-dimethyl-3H,9H-furo[2',3', 4':4,5]oxireno[2,3]naphtho[2,1-c]pyridine-4,9-dione To a stirred solution of [5bS-(1aR*,5bβ,8aα,8bα,10aα, 10bβ)]-5b,6,7,8,8a,8b, 10a, 10b-octahydro-2-hydroxy-5b, 8a-dimethyl-2H,4H,9H -furo[2',3',4':4,5]oxireno[2,3] naphtho[2,1-c]pyran-4,9-dione (prepared from [2S-(1aR* ,2α,5bβ,8aα,8bα,10aα,10bβ)]-5b,6,7,8,8a,8b,10a,10b-octahydro-2-methoxy-5b,8a-dimethyl-2H,4H,9H-furo[2',3', 4':4,5]oxireno[2,3]naphtho[2,1-c]pyran-4,9-dione by hydrolysis; 30.0 mg, 0.10 mmol) and benzylamine (12.9 mg, 0.2 mmol) in dry MeOH (2.0 ml) was added $NaBH_3CN$ (12.6 mg, 0.20 mmol) in one portion at room temperature. After a few drops of acetic acid was added from a Pasteur pipette, the reaction mixture was stirred at room temperature overnight. The reaction mixture was concentrated in vacuo at a bath temperature below 30° C. The residue was directly subjected to preparative TLC [Merck Kieselgel 60, Art 5,744, 0.5 mm thick, ×2; development: n-hexane-AcOEt (1:2); elution: $CH_2Cl_2$—MeOH (10:1), approximate 110 ml] to give [5bS-(1aR*,5bβ,8aα,8bα,10aα,10bβ)]-1a,2,5b,6,7, 8,8a,8b, 10a,10b-decahydro-3-(phenylmethyl)-5b,8a-dimethyl-3H,9H-furo[2',3',4':4,5]oxireno[2,3]naphtho[2,1-c]pyridine-4,9-dione as a colorless solid (30.7 mg, 81.0%): $^1$H-NMR (270 MHz) d($CDCl_3$)7.40~7.25 (m, 5H), 6.04 (s, 1H), 4.92 (dd, J=4.4, 1.2 Hz, 1H), 4.78 (d, J=15.0 Hz, 1H), 4.62 (d, J=15.0 Hz, 1H), 3.89 (d, J=13.9 Hz, 1H), 3.74 (d, J=1.2 Hz, 1H), 2.94 (d, J=13.9 Hz, 1H), 2.29~2.18 (m, 1H), 1.85 (d, J=4.4 Hz, 1H), 1.80~1.40 (m, 4H), 1.27 (s, 3H), 1.10 (s, 3H) ppm; MS (70 eV) m/z 379 (100%, M$^+$), 336 (17.2%),305 (21.9%), 275 (27.8%), 254 (47.8%), 214 (27.1%), 149 (19.7%), 132 (27.6%), 106 (99.8%), 91 (99.1%, C$_7$H$_7^+$).

Example Nine

Preparation of [5bS-(1aR*,5bβ,8aα,8bα,10aα, 10bβ)]-1a,2,5b,6,7,8,8a,8b,10a,10b-decahydro-3-propyl-5b,8a-dimethyl-3H,9H-furo[2',3',4':4,5] oxireno[2,3]naphtho[2,1-c]pyridine-4,9-dione To a stirred solution of [5bS-(1aR*,5bβ,8aα,8bα,10aα, 10bβ)]-5b,6,7,8,8a,8b, 10a, 10b-octahydro-2-hydroxy-5b, 8a-dimethyl-2H,4H,9H-furo[2',3',4':4,5]oxireno[2,3] naphtho[2,1-c]pyran-4,9-dione (prepared from [2S-(1aR*, 2α,5bβ,8aα,8bα,10aα,10bβ]-5b,6,7,8,8a,8b,10a,10b-octahydro-2-methoxy-5b,8a-dimethyl-2H,4H,9H-furo[2',3', 4':4,5]oxireno[2,3]naphtho[2,1 -c]pyran-4,9-dione by hydrolysis; 30.0 mg, 0.10 mmol) and propylamine (8.9 mg, 0.15 mmol) in dry MeOH (3.0 ml) was added NaBH$_3$CN (15.7 mg, 0.25 mmol) in one portion, followed by a few drops of acetic acid from a Pasteur pipette, at room temperature. The reaction mixte was stirred at room temperature for three nights. The reaction mixture was concentrated in vacuo at a bath temperature below 40° C. The residue was partitioned between AcOEt and water. The AcOEt layer was washed withdilute HCl aqueous solution (×1), water (×1), sat. NaHCO$_3$ aqueous solution (×1), and saturated NaCl aqueous solution (×1), dried (MgSO$_4$), and concentrated in vacuo to give a colorless syrup (34.7 mg). This was purified by preparative TLC [Merck Kieselgel 60, Art 5,744, 0.5 mm thick, ×1; development: AcOEt-n-hexane (2:1); elution, CH$_2$Cl$_2$—MeOH (10:1)] to give [5bS-(1aR*,5bβ,8aα,8aα, 10aα,10bβ)]-1a,2,5b,6,7,8,8a,8b,10a,10b-decahydro-3-propyl-5b,8a-dimethyl-3H,9H -furo[2',3',4':4,5]oxireno[2,3] naphtho[2,1-c]pyridine4,9-dione (24.5 mg, 74.7%) as a colorless solid: $^1$H-NMR (270 MHz) d(CDCl$_3$): 5.97 (s, 1H), 4.95 (dd, J=4.4, 1.5 Hz, 1H), 4.02 (d, J=13.9 Hz, 1H), 3.82 (d, 3=1.5 Hz, 1H), 3.53 (dt, J=13.6, 7.1 Hz, 1H), 3.31 (dt, J=13.6, 7.1 Hz, 1H), 3.00 (d, J=13.9 Hz, 1H), 2.29~2.16 (m, 1H), 1.85 (d, J=4.4 Hz, 1H), 1.80~1.40 (m, 7H), 1.28 (s, 3H), 1.25 (s, 3H), 0.93 (t, J=7.5 Hz, 3H) ppm; MS (70 eV) m/z 331 (64.0%, M$^+$), 316 (30.3%, M$^+$-Me'), 303 (84.1%), 275 (27.8%), 302 (93.1%, M$^+$-Et'), 301 (97.7%), 206 (100%).

Example Ten

Preparation of [5bS-(1aR*,5β,8aα,8bα,10aα, 10bβ)]-1a,2,5b,6,7,8,8a,8b,10a,10b-decahydro-5b, 8a-dimethyl-3H,9H-furo[2',3',4':4,5]oxireno[2,3] naphtho[2,1-c]pyridine-4,9-dione To a stirred solution of [5bS-(1aR*,5bβ,8aα,8bα,10aα, 10bβ)]-5b,6,7,8,8a,8b,10a, 10b-octahydro-2-hydroxy-5b, 8a-dimethyl-2H,4H,9H-furo[2',3',4':4,5]oxireno[2,3] naphtho[2,1-c]pyran-4,9-dione (prepared from [2S-(1aR*, 2α,5bβ,8aα,8bα,10aα,10bβ)]-5b,6,7,8,8a,8b, 10a,10b-octahydro-2-methoxy-5b,8a-dimethyl-2H,4H,9H-furo[2',3', 4':4,5)oxireno[2,3]naphtho[2,1-c]pyran-4,9-dione by hydrolysis; 30.0 mg, 0.10 mmol), NaBH$_3$CN (15.7 mg, 0.25 mmol), and ammoniun acetate (11.6 mg, 0.15 mmol) in dry MeOH (3.0 ml) was added two drops of acetic acid from a Pasteur pipette at room temperature. The homogeneous reaction miixture was stirred at room temperature overnight. The reaction mixture was concentrated in vacuo. The syrupy residue was partitioned between AcOEt and dilute HCl aqueous solution. The AcOEt layer was washed with dilute HCl aqueous solution (×2), and saturated NaCl aqueous solution (×2), dried (MgSO$_4$), and concentrated in vacuo to give a white solid (29.9 mg). This was suspended in dry toluene (5.0 ml), and heated at reflux for an hour. After the solvent toluene was evaporated in vacuo, the white solid residue was dissolved in hot tert-butyl alcohol (6.0 ml) again. The resultant mixture was stirred and heated at reflux overnight, and then concentrated in vacuo. The residue was subjected to preparative TLC [Merck Kieselgel 60, Art 1.05774, 0.5 mm thick, ×2; development: CH$_2$Cl$_2$—MeOH (20:1); elution: CH$_2$Cl$_2$—MeOH (10:1)] to give [5bS-(1aR*,5bβ,8aα,8bα,10aα,10bβ)]-1a,2,5b,6,7,8,8a,8b,10a, 10b-decahydro-5b,8a-dimethyl-3H,9H-furo[2',3',4':4,5] oxireno[2,3]naphtho[2,1-c]pyridine-4,9-dione as a colorless solid (7.2 mg, 24.9%), which was a 1:1 mixture of rotamors as shown by $^1$H-NMR (270 MHz) d(CDCl$_3$) 5.96 (s, 0.5H), 5.91 (s, 0.5H), 4.95 (dd, J=4.4, 1.2 Hz, 0.5 Hz), 4.87 (d, J=4.4 Hz, 0.5 Hz), 4.58 (d, J=15.0 Hz, 0.5H), 3.91 (d, J=1.2 Hz, 0.5H), 3.90 (d, J=13.2 Hz, 0.5H), 3.62 (s, 0.5H), 3.61 (d, J=15.0 Hz, 0.5H), 3.56 (d, J=13.2 Hz, 0.5H), 2.37~2.15 (m, 1H), 1.86 (d, J=4.4 Hz, 0.5H), 1.82~1.25 (m, 6H), 1.60 (d, J=4.4 Hz, 1H), 1.25 (s, 1.5H), 1.21 (br.s, 3H), 1.11 (s, 1.5H) ppm; MS (70 eV) m/z 289 (100%, M$^+$).

Example Eleven

Preparation of [3aS-(3aα,5aα,6α,7α,10bβ,10cα)]-1, 2,3,3a,5a,6,6a,7,10b,10c-decahydro-6-hydroxy-6a-(2-ethoxycarbonyl-1-ethylthio)-7-methoxy-3a,10b-dimethyl-4H,9H-furo[2',3',4':4,5]naphtho [2,1-c] pyran-4,9-dione To a stirred solution of [2S-(1aR*,2α,5bβ,8aα,8bα,10aα, 10bβ)]-5b,6,7,8,8a,8b,10a,10b-octahydro-2-methoxy-5b, 8a-dimethyl-2H,4H,9H-furo[2',3',4':4,5]oxireno[2,3] naphtho[2,1-c]pyran-4,9-dione (30.0 mg, 0.094 mmol) and ethyl 3-mercaptopropionate (0.18 ml, d1.039, 1.40 mmol) in dry CH$_2$Cl$_2$(3.0 ml) was added boron trifluoride diethyl etherate (four drops from a pasteur pipette) at room temperature. After stifring at room temperature overnight, the reaction mixture was ice-cooled, and basified with 10% NaOH aqueous solution. The layers were separated. The CH$_2$Cl$_2$ layer was dried (MgSO$_4$), and concentrated in vacuo to give a white solid (88.8 mg). This was subjected to preparative TLC [Merck Kieselgel 60, Art 1.05744, 0.5 mm thick, ×2; development: n-hexane-AcOEt (2:1); elution: CH$_2$Cl$_2$—MOH (10:1)] to give [3aS-(3aα,5aα,6α,7α,10bβ, 10cα)]-1,2,3,3a,5a,6,6a,7,10b,10c-decahydro-6-hydroxy-6a-(2-ethoxycarbonyl-1-ethylthio)-7-methoxy-3a,10b-dimethyl-4H,9H-furo[2',3',4':4,5]naphtho[2,1-c]pyran-4,9-dione as a white solid (54.2 mg, quantitative): $^1$H-N (270

MHz) d(CDCl₃) a major epimer at C-8, 5.73 (s, 1H),5.49 (s, 1H), 5.03 (dd, J=6.4, 4.8 Hz, 1H), 4.59 (dd, J=5.9, 4.8 Hz, 1H), 5.28 (q, J=7.1 Hz, 2H), 3.91 (d, J=6.4 Hz, 1H), 3.57 (s, 3H), 3.27 (ddd, J=12.6, 8.3, 6.4 Hz, 1H), 3.12 (ddd, J=12.6, 6.3, 6.3 Hz, 1H), 2.54 (ddd, J=16.9, 8.3, 6.4 Hz, 1H), 2.36~2.21 (m, 1H), 1.84 (d, J=5.9 Hz, 1H, 1.80~1.57 (m, 3H), 1.47~1.33 (m, 2H), 1.27 (s, 3H), 1.27 (t, J=7.1 Hz, 3H), 1.20 (s, 3H) ppm; MS m/z 454 (1.5%, M⁺), 423 (11.4%, M⁺-OMe'), 422 (13.6%), 322 (100%).

Example Twelve

Preparation of [3aS-(3aα,5aα,6α,10bβ,10cα)]-1,2,3, 3a,5a,6,6a,7,10b,10c-decahydro-6-hydroxy-6a,7-di-(2-propylthio)-3a,10b-dimethyl-4H,9H-furo[2',3', 4':4,5]naphtho[2,1-c]pyran-4,9-dione and [3aS-(3aα, 5aα,6α,7α,10bβ,10cα)]1,2,3,3a,5a6,6a,7,10b,10c-decahydro-6-hydroxy-6a-(2-propylthio)-7-methoxy-3a,10b-dimethyl-4H,9H-furo[2',3',4':4,5]naphthol[2, 1-c]pyran-4,9-dione To a stirred solution of [2S-(1aR*,2α,5bβ,8aα,8bα,10aα, 10bβ)]-5b,6,7,8,8a,8b,10a,10b-octahydro-2-methoxy-5b, 8a-dimethyl-2H,4H,9H-furo[2',3',4':4,5]oxireno[2,3]naphtho[2,1-c]pyran-4,9-dione (28.0 mg, 0.087 mmol) and 2-propanethiol (0.10 ml, d0.82, 1.08 mmol) in dry CH₂Cl₂ (3.0 ml) was added boron trifluoride diethyl etherate (two drops from a pasteur pipette) at room temperature. After stirring at room temperature overnight, the reaction mixture was ice-cooled, and basified with 10% NaOH aqueous solution. The layers were separated. The CH₂Cl₂ layer was dried (MgSO₄), and concentrated in vacuo to give a white solid (38.0 mg). This was purified by preparative TLC [Merck Kieselgel 60, Art 1.05744, 0.5 mm thick, ×2; development: n-hexane-AcOEt (3:2); elution: CH₂Cl₂—MOH (10:1)] to give [3aS-(3aα,5aα,6aα,10bβ,10cα)]-1,2,3,3a,5a, 6,6a,7,10b,10c-decahydro-6-hydroxy-6a,7-di-(2-propylthio)-3a,10b-dimethyl-4H,9H-furo[2',3',4':4,5]naphtho[2,1-c]pyran4,9-dione as a less polar product (10.1 mg, 26.3%): 1H-NMR (270 MHz) d(CDCl₃) 5.76 (s, 1H), 5.73 (s, 1H), 5.16 (dd, J=9.2,4.4 Hz, 1H), 4.72 (dd, J=5.5, 4.4 Hz, 1H), 3.55 (hept, J=6.8 Hz, 1H), 3.38 (hept, J=6.8 Hz, 1H), 3.22 (ddd, J=15.0, 4.6, 4.6 Hz, 1H), 3.02 (d, J=9.2 Hz, 1H), 2.03 (d, J=5.5 Hz, 1H), 1.88~1.55 (m, 4H), 1.50~1.35 (m, 1H), 1.39, 1.37, and 1.33 (each d, J=6.8 Hz, total, 12H), 1.31 (s, 3H, 1.24 (s, 3H) ppm; MS m/z 440 (0.15%, M⁺), 365 (22.7%), 323 (18.2%), 295 (100%); and [3aS-(3aα,5aα,6α, 7α,10bβ,10cα)]-1,2,3,3a,5a,6,6a,7,10b,10c-decahydro-6hydroxy-6a-(2-propylthio)-7-methoxy-3a, 10b-dimethyl4H,9H-furo[2',3',4':4,5]naphtho[2,1-c]pyran-4,9-dione as a more polar product (21.1 mg, 61.2%): ¹H-NMR (270 MHz) d(CDCl₃): 5.71 (s, 1H), 5.51 (s, 1H), 5.00 (dd, J=6.2, 4.8 Hz, 1H), 4.58 (dd, J=5.9, 4.8 Hz, 1H), 3.56 (s, 3H), 3.41 (hept, J=7.0 Hz, 1H), 3.07~2.95 (m, 1H), 2.30 (ddd, J=14.7, 4.8, 4.8 Hz, 1H), 1.85 (d, J=5.9 Hz, 1H), 1.80~1.55 (m, 4H), 1.48~1.35 (m, 3H), 1.35 (d, J=7.0 Hz, 3H), 1.31 (d, J=7.0 Hz, 3H), 1.27 (s, 3H), 1.24 (s, 3H) ppm; MS m/z: 396 (0.4%, M⁺), 336 (50.8%), 295 (100%), 294 (98.4%), 293 (96.2%).

Example Thirteen

Preparation of [2aS-(1aR*,2aβ,5aα,5bα,7aα,7bβ)]-2a,3,4,5,5a,5b,7a,7b-octahydro-1a-{2-methoxycarbonyl-1-(E)-ethenyl}-2a,5a-dimethyl-1aH,6H-furo[2',3',4':4,5]oxireno[2,3]-(E)-(1-naphthalenylidene)acetic acid-6-one To a stirred mixture of [5bS-(1aR*,5bβ,8aα,8bα,10aα, 10bβ)]-5b,6,7,8,8a,8b, 10a, 10b-octahydro-2-hydroxy-5b, 8a-dimethyl-2H,4H,9H-furo[2',3',4':4,5]oxireno[2,3]naphtho[2,1-c]pyran-4,9dione (prepared from [2 S-(1aR*, 2α,5bβ,8aα,8bα,10aα,10bβ)]-5b,6,7,8,8a,8b,10a,10b-octahydro-2-methoxy-5b,8a-dimethyl-2H,4H,9H-furo[2',3', 4':4,5]oxireno[2,3]naphtho[2,1-c]pyran-4,9-dione by hydrolysis; 60.0 mg, 0.20 mmol), lithium chloride (anhydrous, 30.0 mg, 0.71mmol), trimethyl phosphonoacetate (0.11 ml, d1.125, 0.71 mmol), and dry acetonitrile (4.0 ml) was added 1,8-diazabicyclo[5.4.0]undec-7-ene (0.09 ml, d1.018, 0.59 mmol) in one portion at room temperature. The resultant homogeneous pale yellow reaction mixture was stirred at room temperature for four nights. The reaction mixture was partioined between AcOEt and 1.0M HCl aqueous solution. The AcOEt layer was separated, and washed with saturated NaCl aqueous solution (×1), dried (MgSO₄) and concentrated in vacuo to give a pale yellow syrup (0.135 g). This was subjected to preparative TLC [Merck Kieselgel 60, Art 1.05744, 0.5 mm thick, ×2; development: CH₂Cl₂—MeOH (10:1); elution: CH₂Cl₂—MOH (10:1)] to give a colorless syrup (28.3 mg). This was purified again by preparative TLC under the same conditions as described above to give [2aS-(1aR*,2aβ,5aα,5bα,7aα, 7bβ)]-2a,3,4,5,5a,5b,7a,7b-octahydro-1a-{2-methoxycarbonyl-1-(E)-ethenyl}-2a,5a-dimethyl- 1aH,6H-furo[2',3',4':4,5]oxireno[2,3]-(E)-(1-naphthalenylidene) acetic acid-6-one as a colorless foam (18.6 mg, 26.2%): ¹H-NMR (270 MHz) d(CDCl₃): 6.83 (d, J=16.1, 1H), 5.97 (s, 1H), 5.94 (d, J=16.1 Hz, 1H), 4.91 (d, J=4.4 Hz, 1H), 3.74 (s, 3H), 3.61 (s, 1H), 3.10 (br.s, 1H), 2.31 (dm, J=14.7 Hz, 1H), 1.80~1.57 (m, 3H), 1.68 (d, J=4.4 Hz, 1H), 1.50~1.23. (m, 2H), 1.24 (s, 3H), 1.10 (s, 3H) ppm; MS m/z 362 (5.7%, M⁺), 344 (13.6%), 331 (57.2%), 330 (99.0%), 329 (100%).

Example Fourteen

Preparation of butyl [2aS-(1aR*,2aβ,5aα,5bα,7aα, 7bβ)]-2a,3,4,5,5a5b,7a,7b-octahydro-1a-(di-butoxymethyl)-2a,5a-dimethyl-1aH,6H-furo-[2', 3'4':4,5]oxireno[2,3]-(E)-(1-naphthalenylidene) acetate-6-one A mixture of [2S-(1aR*,2α,5bβ,8aα,8bα,10aα,10bβ)]-5b,6,7,8,8a,8b,10a,10b-octahydro-2-methoxy-5b,8a-dimethyl-2H,4H,9 H-furo[2',3',4':4,5]oxireno[2,3]naphtho[2,1-c]pyran-4,9-dione (30.0 mg, 0.094 mmol), pyridinium p-toluenesulphonate (a few flakes), and n-butyl alcohol (5.0 ml) was stirred and heated at reflux. The solid [2S-(1aR* ,2α,5bβ,8aα,8bα, 10aα,10bβ)]-5b,6,7,8,8a,8b,10a,10b-octahydro-2-methoxy-5b,8a-dimethyl-2H,4H,9H-furo[2',3', 4':4,5]oxireno[2,3]naphtho[2,1-c]pyran-4,9-dione became dissolved with heating. After the stirring was continued with heating at reflux overnight, the reaction mixture was concentrated in vacuo. The yellow residue was diluted with AcOEt. The AcOEt solution was washed with water (×1), and saturated NaCl aqueous solution (×1), dried (MgSO₄), and concentrated in vacuo to give a pale yellow syrup (59.5 mg). This was subjected to preparative TLC [Merck Kieselgel 60, Art 1.05744, 0.5 mm thick, ×2; development: n-hexane-AcOEt (2:1); elution: CH₂Cl₂—MOH (10:1), 110 ml] to give butyl [2aS-(1aR*,2aβ,5aα,5bα,7aα,7bβ)]-2a,3,4,5,5a,5b,7a,7b-octahydro-1a-(di-butoxymethyl)-2a,5a-dimethyl-1aH,6H-furo-[2',3',4':4,5]oxireno[2,3]-(E)-(1-naphthalenylidene)acetate-6-one as a colorless syrup (41.7 mg, 90.0%): $^1$H-NMR (270 MHz) d(CDCl$_3$) 5.83 (s, 1H), 5.19 (s, 1H), 4.86 (d, J=4.4 Hz, 1H), 4.25~4.08 (m, 2H), 3.99 (s, 3H), 3.78~3.58 (m, 3H), 3.27 (dt, J=9.2, 6.6 Hz, 1H), 2.29 (dm, J=14.3 Hz, 1H), 1.80~1.50 (m, 6H), 1.50~1.15 (m, 8H), 1.20 (s, 3H), 1.10 (s, 3H), 0.95 (t, J=7.3 Hz, 3H), 0.93 (t, J=7.0 Hz, 3H), 0.86 (t, J=7.3 Hz, 3H) ppm; MS m/z 492 (0.30%, M$^+$), 419 (37.1%), 288 (74.2%), 159 (100%).

the chemical structures of the compounds prepared in the working example are summarized in the following Table.

TABLE

| | | atoms | | | | | | | | bonds | | | |
|---|---|---|---|---|---|---|---|---|---|---|---|---|---|
| Ex. # | R$^1$ | X | R$^2$ | R$^3$ | R$^4$ | R$^5$ | R$^6$ | R$^7$ | R$^8$ | X-C$^4$ | R$^1$-C$^2$ | C$^1$-C$^{14}$ | C$^5$-C$^6$ |
| 1 | O | O | — | H | a) | | ox | | lac | sb | db | db | sb |
| 1 | O | O | — | H | a) | — | H | | lac | sb | db | db | db |
| 1 | O | O | — | H | H | — | H | | lac | sb | db | db | db |
| 1 | O | O | — | OH | OH | — | H | | lac | sb | db | db | db |
| 1 | O | O | — | OH | OH | | ox | | lac | sb | db | db | sb |
| 1 | O | O | — | H | H | — | H | H | OH | sb | db | db | db |
| 2 | O | O | — | H | H | | ox | | lac | sb | db | db | sb |
| 3 | O | O | — | H/b) | | | ox | | lac | sb | db | db | sb |
| 4 | O | O | — | H | a) | | ox | | lac | sb | db | db | sb |
| 5 | O | O | — | H | a) | H | OH | | lac | sb | db | sb | sb |
| 5 | O | O | — | H | a) | | ox | | lac | sb | db | sb | sb |
| 6 | OH | — | — | H/OH | | | ox | | lac | — | sb | db | sb |
| 7 | O | O | — | H | a) | H | OH | | lac | sb | db | db | sb |
| 8 | O | N | c) | H | H | | ox | | lac | sb | db | db | sb |
| 9 | O | N | d) | H | H | | ox | | lac | sb | db | db | sb |
| 10 | O | N | H | H | H | | ox | | lac | sb | db | db | sb |
| 11 | O | O | — | H | a) | e) | OH | | lac | sb | db | db | sb |
| 12 | O | O | — | f)/H | | f) | OH | | lac | sb | db | db | sb |
| 12 | O | O | — | H | a) | f) | OH | | lac | sb | db | db | sb |
| 13 | O | O | H | H | g) | | ox | | lac | — | db | db | sb |
| 14 | O | O | h) | i) | i) | | ox | | lac | — | db | db | sb | a) methoxy; b) CH$_3$OC(O)CH$_2$-; c) benzyl; d) propyl; f) isopropylthio g) B6; h)butyl; i) butoxy ox: oxirane; lac: lactone; sb: single bond db: double bond

What is claimed is:

1. A method for the treatment of IL-1 and TNF mediated diseases of a subject in need of such treatment which comprises administering to said subject an anti-inflammatory amount of a compound of the formula

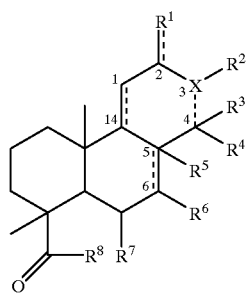

(I)

wherein the dotted line is an optional bond;

R$^1$ is O or OH;
X is O ot N, or absent;
R$^2$ is H, OH, C$_1$-C$_5$ alkyl or benzyl, or absent;
R$^3$ is H, OH, C$_1$-C$_4$ alkoxycarbonyl-C$_1$-C$_4$ alkyl, C$_1$-C$_4$ alkoxycarbonyl-C$_1$-C$_3$ alkenyl, C$_1$-C$_4$ alkoxy or C$_1$-C$_4$ alkylthio;
R$^4$ is H or C$_1$-C$_5$ alkoxy;
R$^5$ is H, C$_1$-C$_4$ alkylthio or C$_1$-C$_4$ alkoxycarbonyl-C$_1$-C$_4$ alkylthio, or absent;
R$^6$ is H or OH; or
R$^5$ and R$^6$ form, together with the carbon atom to which they are attached, an oxirane ring;
R$^7$ is H;
R$^8$ is OH; or
R$^7$ and R$^8$ form, together with the carbon to which they are attached, a lactone ring; with proviso that when X and O and R$^2$ is absent, the dotted line between 3- and 4-position is a single bond;
and a pharmaceutically acceptable carrier.